United States Patent [19]
Williamson, IV et al.

[11] Patent Number: 5,891,160
[45] Date of Patent: Apr. 6, 1999

[54] FASTENER DELIVERY AND DEPLOYMENT MECHANISM AND METHOD FOR PLACING THE FASTENER IN MINIMALLY INVASIVE SURGERY

[75] Inventors: Warren P. Williamson, IV, Loveland, Ohio; George T. Christakis, Toronto, Canada; Paul Spence, Louisville, Ky.; Thomas Ward; Douglas P. Allen, both of Grandview, Ohio

[73] Assignee: CardioVascular Technologies, LLC, Loveland, Ohio

[21] Appl. No.: 985,355

[22] Filed: Dec. 4, 1997

Related U.S. Application Data

[63] Continuation-in-part of Ser. No. 802,948, Feb. 21, 1997, which is a continuation-in-part of Ser. No. 606,343, Feb. 23, 1996, Pat. No. 5,716,370.

[51] Int. Cl.⁶ .................................................. A61B 17/00
[52] U.S. Cl. ...................... 606/144; 227/176.1; 112/169
[58] Field of Search .................................. 606/232, 142, 606/144, 147, 148, 139, 151, 157, 219, 152, 153; 227/901, 902, 176.1, 19, 116, 169, 80.03; 112/169, 80.03

[56] References Cited

U.S. PATENT DOCUMENTS

| | | | |
|---|---|---|---|
| 5,306,281 | 4/1994 | Beurrier | 606/144 |
| 5,306,301 | 4/1994 | Graf et al. | 623/11 |
| 5,474,568 | 12/1995 | Scott | 606/144 |
| 5,560,532 | 10/1996 | Defonzo et al. | 227/176.1 |

*Primary Examiner*—Michael Buiz
*Assistant Examiner*—Vikki Trinh
*Attorney, Agent, or Firm*—Terry M Gernstein

[57] ABSTRACT

A one-piece fastener or staple includes a base that contacts tissue and a prong that extends through the tissue. A suture lead is anchored to the base and a needle is attached to the suture lead. A tool positions the fastener adjacent to the tissue, and is operated to drive the prong and the suture needle through the tissue. The tool includes a needle grabber that is operated to grab the needle and pull the needle out of the patient. Since the suture lead is attached to the fastener, a prosthesis can be placed on the suture lead and pushed down to the tissue. A cassette is releasably mounted on the tool and contains the fastener, the suture lead and the suture needle. Alternative forms of the anchor have sutures attached to a base at locations that are spaced apart from each other, and sutures associated with each of two adjacent anchors can be tied together or sutures associated with a single anchor can be tied together. A suture threadably connected to an anchor can be used as a running suture. A prosthetic device can have a running suture associated therewith that is threadably attached to each of a plurality of anchors. Another form of the system includes a running suture with loops that can have additional anchors attached thereto as needed if the surgeon decides to add further anchors to the system to customize the system to the particular patient.

21 Claims, 25 Drawing Sheets

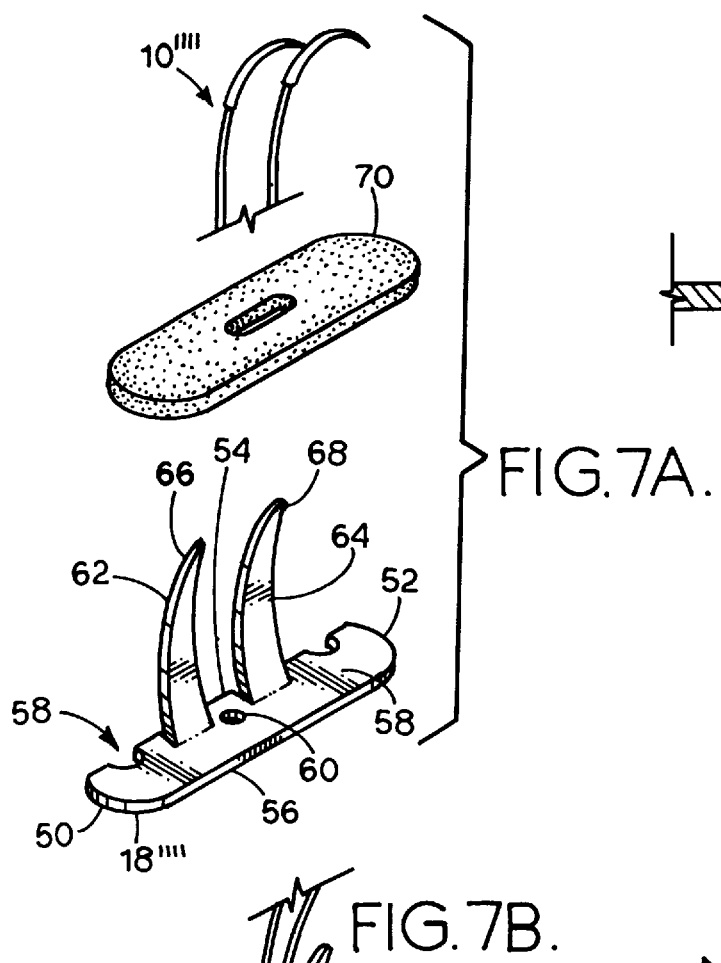
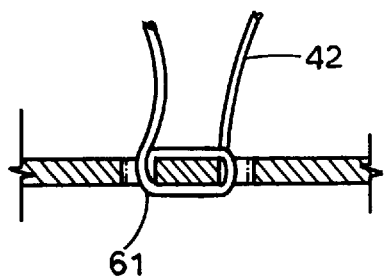
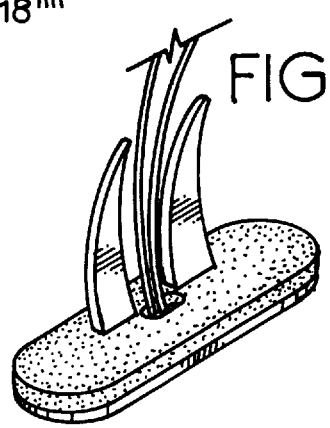
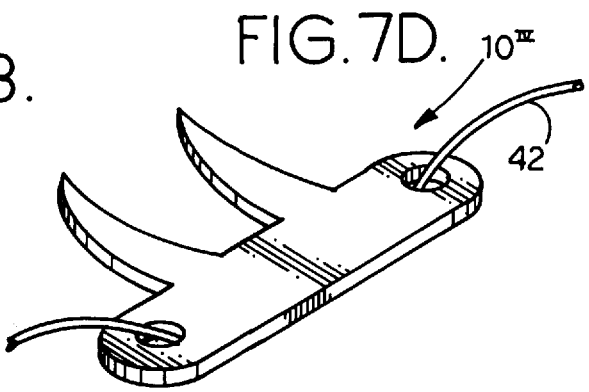

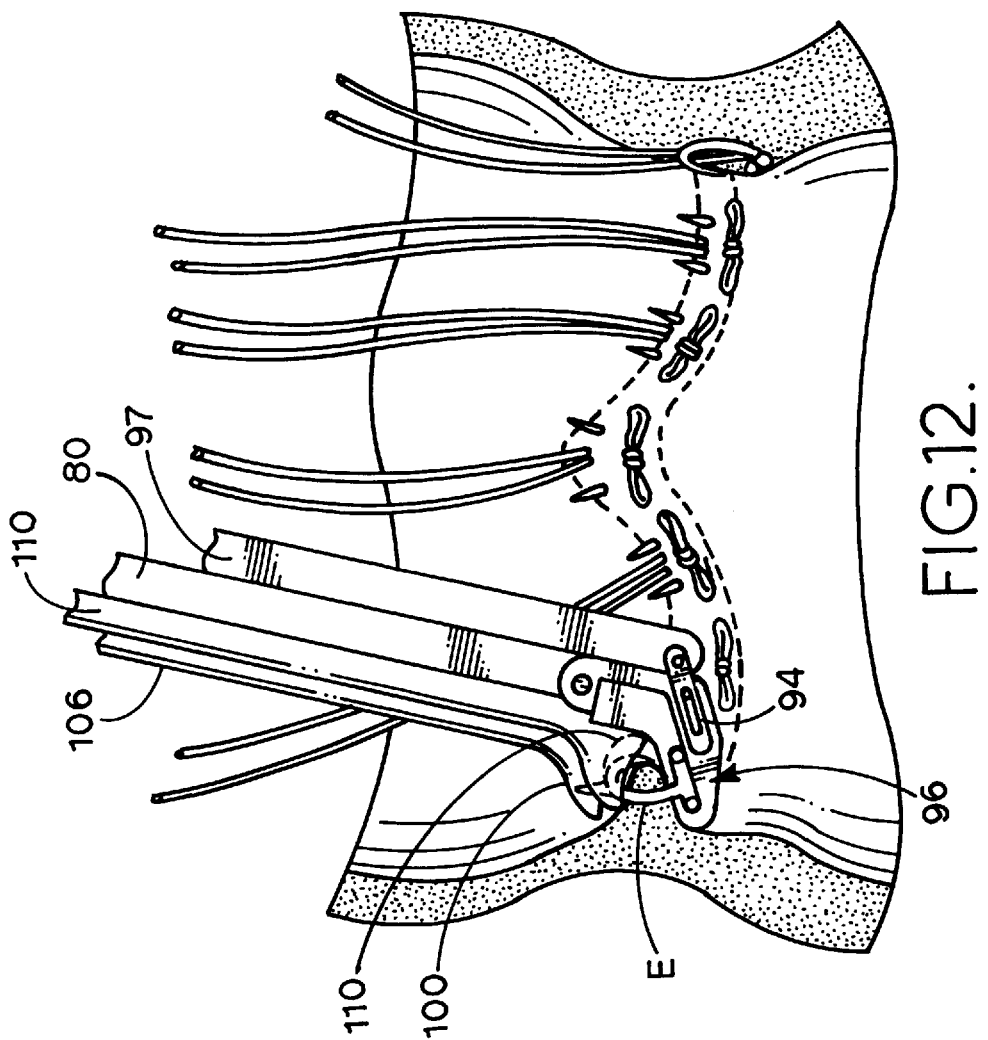

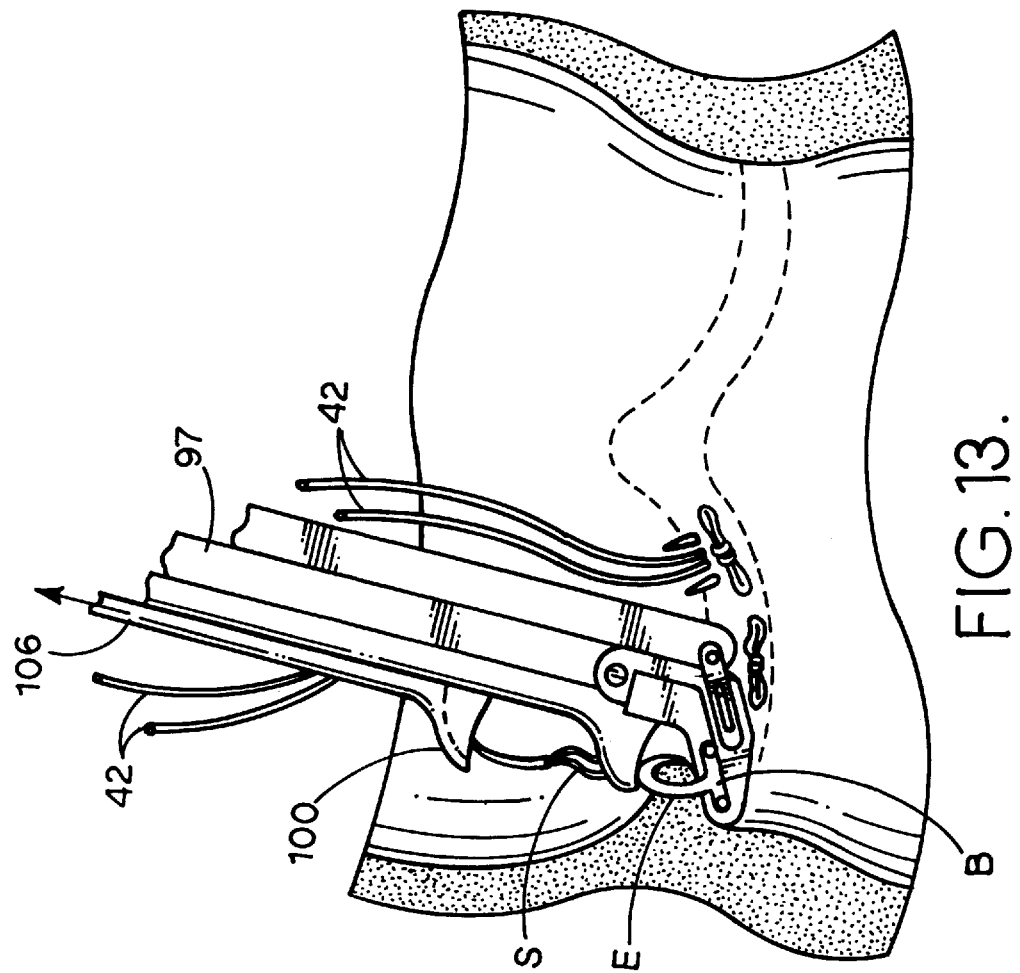

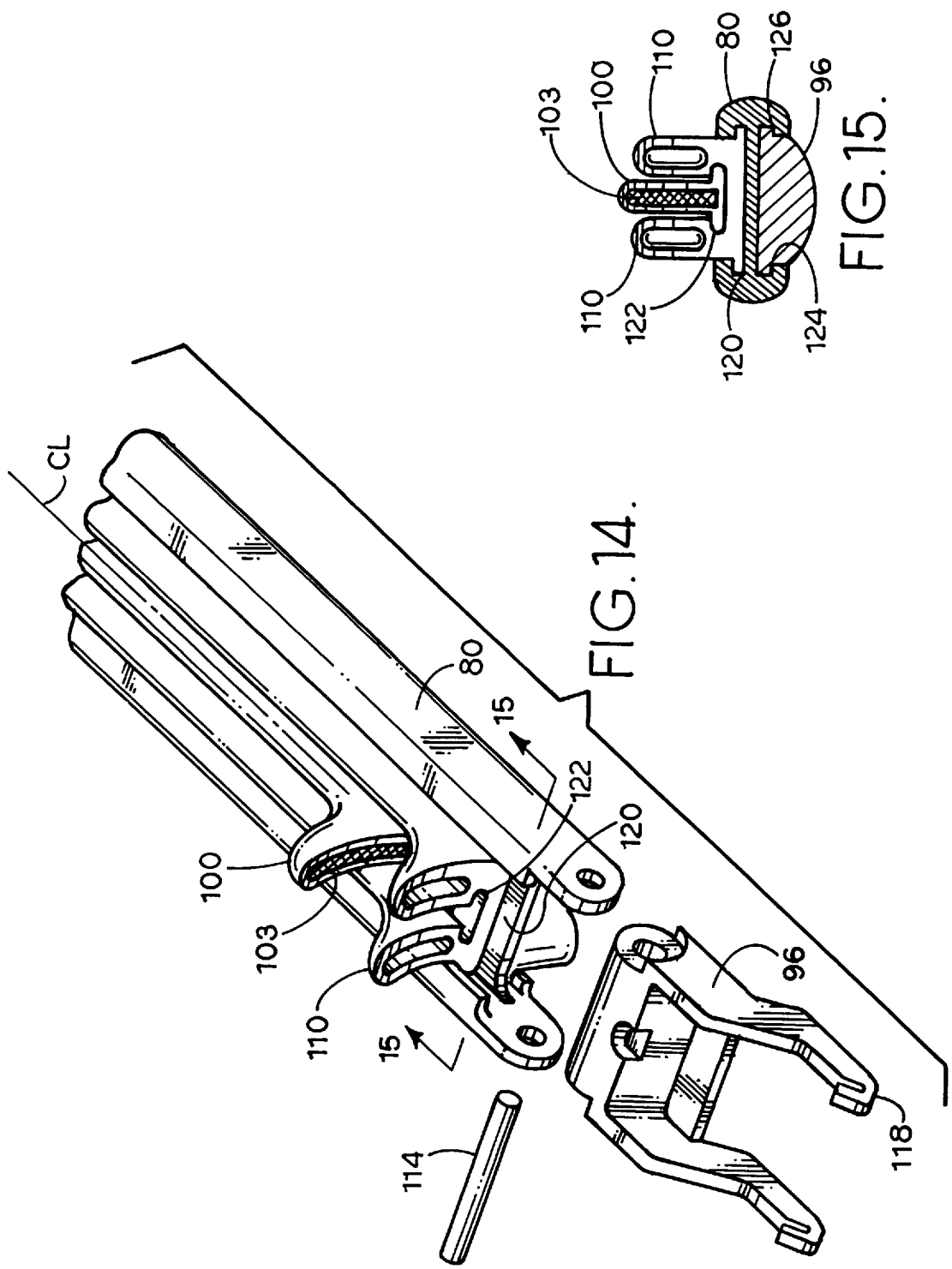

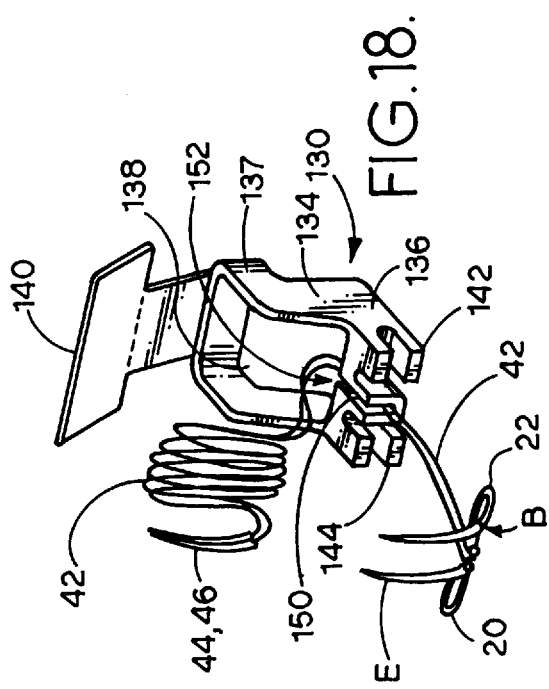
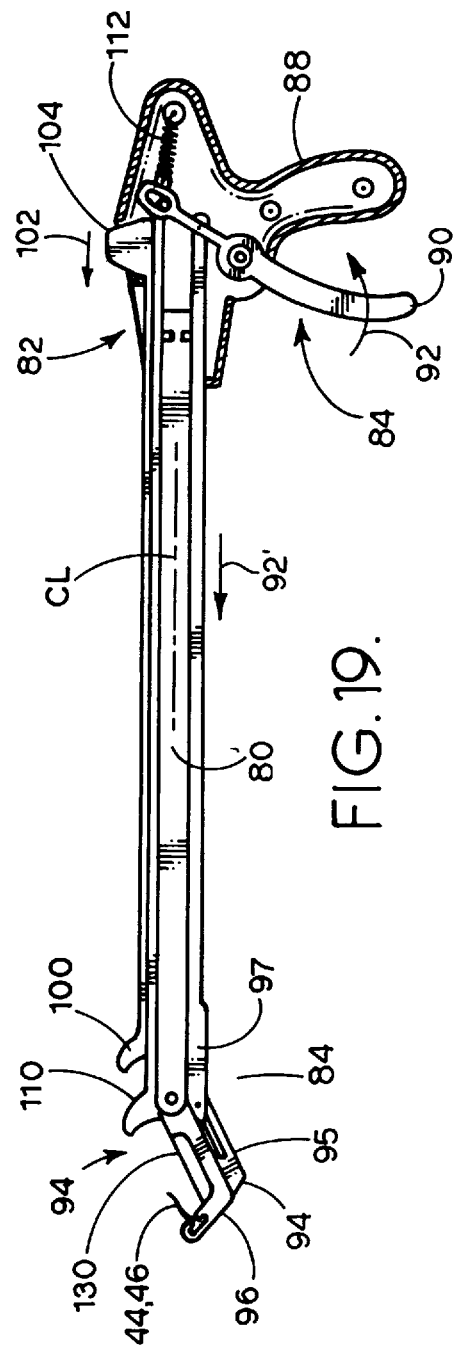

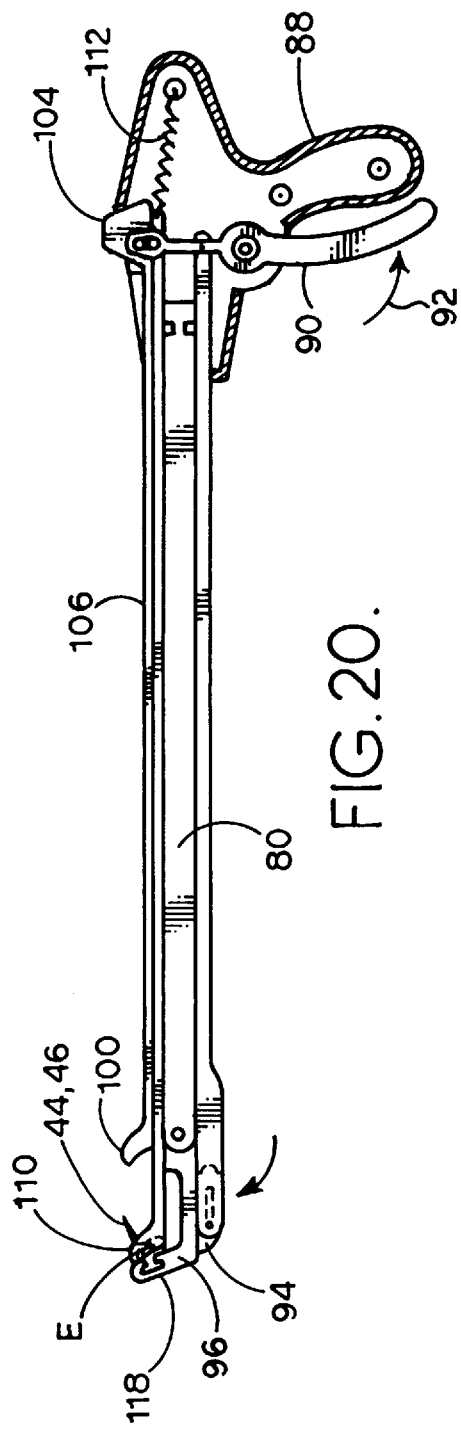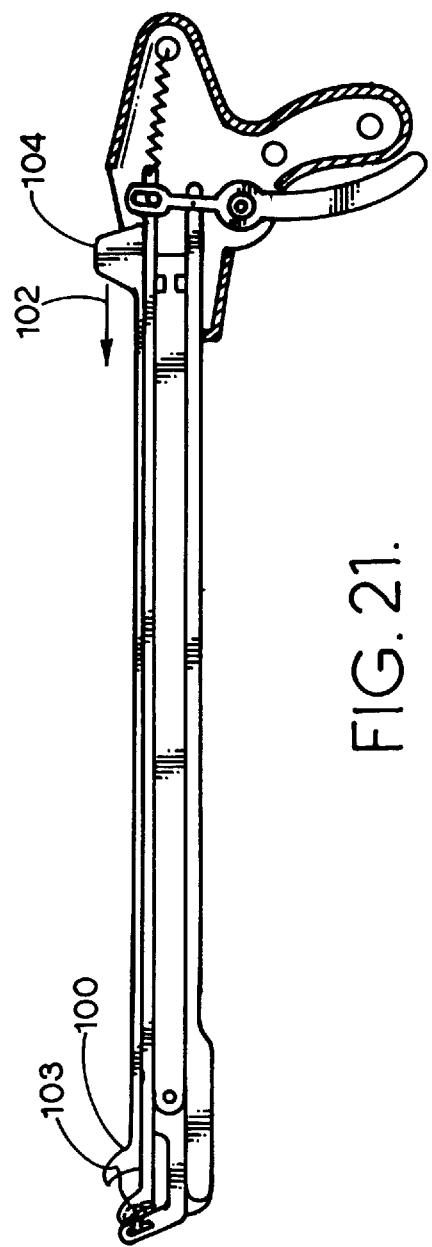
FIG. 20.
FIG. 21.

FASTENER DELIVERY AND DEPLOYMENT MECHANISM AND METHOD FOR PLACING THE FASTENER IN MINIMALLY INVASIVE SURGERY

The present application is a continuation-in-part application of Ser. No. 08/802,948 filed on Feb. 21, 1997 which is a continuation-in-part of application Ser. No. 08/606,343, filed on Feb. 23, 1996, now U.S. Pat. No. 5,716,370.

TECHNICAL FIELD OF THE INVENTION

The present invention relates to the general art of surgery, and to the particular field of minimally invasive surgery, fasteners and tools associated therewith.

BACKGROUND OF THE INVENTION

In recent years, there has been a growing trend toward using minimally invasive surgical techniques to perform heretofore complicated and complex operations. Minimally invasive techniques have therefore been applied to many procedures, such as gall bladder removal, operations on the reproductive organs, urological operations, and more recently, heart valve repair and replacement as well as by-pass operations. Minimally invasive surgery uses only a small incision through which tools are inserted into the patient, with the tool being manipulated from outside the patient. Video is often used so the surgeon can view the surgical site. Minimally invasive surgery has several advantages over other techniques including: less trauma to the patient, smaller incisions, less post-operative pain, quicker recovery time, shorter time spent in the intensive care unit, as well as other advantages that will occur to those skilled in the art.

The nature of minimally invasive surgery demands several criteria that should be considered for any item used in minimally invasive surgery. This disclosure will focus on fasteners and tools used to place fasteners in a minimally invasive surgical technique. Specifically, this disclosure will focus on fasteners and tools used to place fasteners as well as the techniques for using those tools and fasteners in minimally invasive heart valve replacement surgery. For example, the fastener should be capable of expeditious use, with speed being important for many reasons. However, even though speed is important, the fastener must be capable of reliable and secure placement, since a non-secure fastener can have undesirable results. Still further, any item used for minimally invasive surgery, like any item used for any surgery, should have the confidence of the surgeon. This requires any new item to be usable with techniques and tools that are familiar to the surgeon so he or she need not make large changes in a technique they are already familiar with. It has been observed that surgeons are comfortable in making only incremental changes in technique rather than large scale and sweeping changes in technique. In many minimally invasive procedures, access to the surgical site is of paramount concern. The instruments should be designed to have a minimum bulk and to facilitate action that the surgeon can no longer accomplish with his hands due to restricted access. Since the surgeon will have limited access and visualization of the site, it is important that the tools being used facilitate this procedure as much as possible. In addition, since the access is so limited, methods must be effective. There must be a high probability of success in carrying out these techniques for them to be viable and accepted. As mentioned above, heart valve replacement will be used herein as a specific example of a technique that is adaptable to minimally invasive techniques. Heart valve replacement using minimally invasive techniques is fully discussed in co-pending patent application Ser. No. 08/802,948 filed on Feb. 21, 1997 which is a continuation-in-part of co-pending application Ser. No. 08/606,343, filed on Feb. 23, 1996 by the same inventors. The disclosures of these applications are fully incorporated herein by reference. While heart valve replacement will be used as the best mode, it is understood that the invention disclosed in this application can be used in a myriad of techniques as will occur to those skilled in the art based on the teaching of this disclosure. Accordingly, there is no intention to limit the present disclosure to heart valve replacement. Still further, the terms "fastener" and "staple" will be used herein interchangeably. However, those skilled in the art will understand that the term "fastener" can include other elements and a "staple" is a form of fastener.

Currently, heart valves are installed with double lead sutures with a pledget and needles on the end of each suture lead. Each suture needle is independently placed through the annulus of the tissue and the free leads are brought up outside of the cavity. Pairs of these sutures are then placed circumferentially around the annulus where the old valve has been excised. Once all of the sutures are placed the needles are then passed through the sewing cuff on the prosthetic heart valve. The prosthesis heart valve is then slid down the associated suture into place in the annulus and the knots are tied.

Currently, some companies have been making tools to facilitate suturing of heart valves for minimally invasive procedures. These include modifications of existing needle driver (forceps) technology. The problem is that a long tool needed for the minimally invasive access makes it difficult to manipulate the tools and there might be little time savings realized. Surgeons therefore have had a difficult time replicating their current techniques with minimally invasive devices. For instance, when a surgeon places and drives a needle, the path of motion the needle takes through the patient's tissue is on an arc, with the center of the arc determined roughly by the radius of curvature of the needle. In a minimally invasive surgery procedure, one cannot twist the needle driving forceps in the same path as one does when using the "open procedure" instruments. This is due in part to the limited space. Also, this is due to restricted "inline' viewing which is all one can obtain when viewing down a small and narrow tunnel-like incision used in minimally invasive surgical procedures. In addition, some surgeons may, in some procedures, want control of the number of sutures used and the location of each of those sutures. In other words, the procedure will most likely take longer and require greater surgeon skill than would a standard non-minimally invasive operation. This will hamper the growth of minimally invasive procedures.

Therefore, there is a need for a fastener and tool for placing that fastener that will be readily adopted by surgeons practicing minimally invasive surgery, such as heart valve replacement surgery and by-pass surgery.

Still further, it is very undesirable for a suture to come out of the tissue or the item being anchored to the tissue. This can be a problem in older patients with brittle tissue. Therefore, the stress (force per unit area) placed on the tissue by any device used to anchor another device to the patient should be as low as possible. This can be achieved by either reducing the amount of force applied to the tissue or by increasing the area of force application. The amount of force applied may not be easily reduced. Therefore, there is a need for a fastener that can increase the total area of force application in an anchor situation without unduly sacrificing other advantages.

Still further, suturing patterns can be time consuming, and can be difficult. Anything that can shorten the time of a surgical procedure can be advantageous. Therefore, there is a need for a fastener that can be quickly placed yet will still permit a surgeon to have great control of the suturing process and pattern. The suturing pattern can minimize the time a surgeon spends tying off knots as well.

As can be appreciated, the placement of devices in a minimally invasive manner has visibility problems associated therewith. Since the operation is occurring deep inside a patient, and the surgeon is manipulating tools from outside the patient, visibility as well as ease of manipulation are both important issues that should be considered in designing elements that are to be used in minimally invasive surgery.

Therefore, there is a need for a fastener and a tool for placing that fastener that can be as visible as possible during a minimally invasive surgical procedure, yet will be as easy as possible to place and operate.

Still further, since many patients have variations in size and spacing for the tissue to which a prosthetic device is to be anchored, the surgeon may want to add suture anchors to the anchors that are supplied with the device of the present invention. Therefore, some means should be available to permit a surgeon to customize the anchoring features of the system as needed.

OBJECTS OF THE INVENTION

It is a main object of the present invention to provide a surgical fastener that can be used in minimally invasive surgery and which has features that will make it readily acceptable to surgeons practicing minimally invasive surgery.

It is another object of the present invention to provide a surgical fastener and tool for placing that fastener during minimally invasive surgery.

It is another object of the present invention to provide a surgical fastener and tool for placing that fastener during minimally invasive surgery in a secure manner.

It is another object of the present invention to provide a surgical fastener and tool for placing that fastener during minimally invasive surgery which can place the fastener in an accurate and reliable manner It is another object of the present invention to provide a surgical fastener and tool for placing that fastener during minimally invasive surgery which can use known techniques.

It is another object of the present invention to provide a surgical fastener and tool for placing that fastener during minimally invasive surgery which can be used with a minimum number of steps in order to expedite the process.

It is another object of the present invention to provide a surgical fastener and tool for placing that fastener during minimally invasive surgery which includes means for permitting a surgeon to customize the anchoring features of the system as needed.

It is another object of the present invention to provide a surgical fastener and tool for placing that fastener during minimally invasive surgery in which pairs of sutures can be quickly and easily placed.

It is another object of the present invention to provide a surgical fastener and tool for placing that fastener during minimally invasive surgery in which once placed, the fastener has a high pullout strength.

It is another object of the present invention to provide a surgical fastener and tool for placing that fastener during minimally invasive surgery which is adaptable for the minimal access associated with minimally invasive surgery.

It is another object of the present invention to provide a surgical fastener and a tool for placing that fastener during minimally invasive surgery in which a suture anchoring system which reduces the stress placed on either a prosthetic device being placed or on the tissue.

It is another object of the present invention to provide a surgical fastener and a tool for placing that fastener during minimally invasive surgery in which the prosthetic device is as visible as possible during placement and during the completion of the suturing process.

It is another object of the present invention to provide a surgical fastener and a tool for placing that fastener during minimally invasive surgery in which the prosthetic device is as easily placed as possible.

It is another object of the present invention to provide a surgical fastener and a tool and a method therefor for placing that fastener during minimally invasive surgery in which the operating time is substantially reduced and is minimized.

It is another object of the present invention to provide a surgical fastener and a tool and a method therefor for placing that fastener during minimally invasive surgery in which the operating time is substantially reduced and is minimized by minimizing the number of knots required.

It is a specific object of the present invention to provide a surgical fastener and tool for placing that fastener during minimally invasive surgery in which a suture anchoring system gathers a large area of a prosthetic device cuff to be compressed against the patient's tissue to decrease stress placed on both the cuff and on the tissue.

It is a specific object of the present invention to provide a surgical fastener and tool for placing that fastener during minimally invasive surgery in which a fastener is used to secure a loop of suture to the tissue where the loop is free to travel under the fastener.

It is a specific object of the present invention to provide a surgical fastener and tool for placing that fastener during minimally invasive surgery and a method therefor in which a running suture is used to secure a prosthesis to a patient.

It is a specific object of the present invention to provide a surgical fastener and tool for placing that fastener during minimally invasive surgery and a method therefor in which a running suture is used to secure a prosthesis to a patient in which the running suture is placed alternately between fasteners and the prosthetic device.

It is a specific object of the present invention to provide a surgical fastener and tool for placing that fastener during minimally invasive surgery and a method therefor in which the number of sutures used is minimized.

It is a specific object of the present invention to provide a surgical fastener and tool for placing that fastener during minimally invasive surgery in which the fastener has a large surface area in order to spread the suture load over as large an area as possible.

It is another specific object of the present invention to provide a surgical fastener and tool for placing that fastener during minimally invasive surgery in which the suture is anchored to the fastener so the suture and fastener can be expeditiously placed all in one unit.

It is another specific object of the present invention to provide a surgical fastener and tool for placing that fastener during minimally invasive surgery in which the tool is easy to manipulate.

It is another specific object of the present invention to provide a surgical fastener and tool for placing that fastener during minimally invasive surgery in which the tool can be operated to move through an arc during staple placement whereby placement and visualization of such placement is facilitated.

It is another specific object of the present invention to provide a surgical fastener and tool for placing that fastener during minimally invasive surgery which permits the use of known methods for tying a prosthesis to an annulus.

It is another specific object of the present invention to provide a surgical fastener and tool for placing that fastener during minimally invasive surgery which permits the use of sutures to allow many kinds of prostheses to be used, including mechanical or tissue valves.

SUMMARY OF THE INVENTION

These, and other, objects are achieved by a one-piece fastener that is easily set in a minimally invasive surgical technique, yet will be secure once set. The fastener is one-piece with a tissue-engaging area that is large enough to hold the fastener in place, even in older patients where the tissue may be fragile. A tool for placing the fastener is also disclosed.

With the disclosed system, the ability of the surgeon to anchor suture leads to an annulus is improved thereby making the anchoring procedure faster, more accurate and more secure. The suture is attached to a staple which has been placed in the tissue and fastened into the annulus. The placed staple thus anchors the suture leads to the tissue. The staple is releasably mounted on a staple driving portion of the tool. The staple driving device has an articulated arm which allows the staple to be manipulated in along an arcuate path through the tissue. This allows the surgeon to place the points of the staple under the annulus, rotate the head of the device in a wrist-like motion, and thereby bring the points of the staple up through the annulus and exiting above the annulus. Once the points of the staple have exited they can be crimped over by an anvil on the tool thus securing the suture anchoring staple into the annulus in a secure manner. This procedure is faster than the current techniques since no loading and exchanging of needle holding devices is required.

In addition to the staple legs passing through the annulus tissue, a pair of sutures is passed through the annulus between each staple leg in one form of the invention. This then feeds the suture leads through the annulus in much the same path as the legs of the staple would follow. Once the staple has emerged on the outside of the annulus and the staple legs have been crimped over and secured, a second part of the device is manipulated to grab the ends of the needles and pull on the needles. This releases the needles from a disposable cassette releasably mounted on the tool. Suture leads are stored in the cassette, and pay out from inside the cassette until they are brought out of the patient. This then completes the suture anchoring procedure for each pair. Once the suture anchors have been placed peripherally around the annulus, each of the needles and suture leads can be passed through a sewing cuff of a prosthetic heart valve in the manner discussed in the referenced patent application. After this, the valve is placed and the sutures tied in a manner known to those skilled in the art. A knot pusher can be used to tie off the sutures.

An additional advantage of the presently disclosed system is that the crown of the staple is wide and long and can be slightly curved to match the shape of the annulus. Thus, the staple will spread the load of each suture pair over a large area than the prior art even using a felt pledget on a suture. This, in turn, will allow the surgeon to position fewer suture pairs around the periphery of the annulus while still obtaining all of the sealing capabilities of the suture. The large crown of a single staple will seal the annulus tissue against the sewing cuff more effectively than would a pair of sutures. In addition, a pad, or pledget material, could be added to the crown to reduce trauma to fragile tissue.

With standard suture placement, an average 21 mm valve requires between 15 and 18 pairs of sutures to effectively seal the sewing cuff of the prosthesis against the annulus. The amount of sutures necessary to mechanically retain the valve prosthesis in place is far less than that required to ensure that it is actually sealed. Each suture pair when installed with the pledget under the annulus whereby the pledget must be pulled through the tissue in order to rip it out, will withstand approximately 9–12 lbs of pull out force. Therefore, with fifteen pairs of sutures, the amount of force required to rip a valve loose from its tissue would be in the order of 80–180 lbs. Since aortic pressures rarely exceed 120 Hg (which would equate to 1.25 lbs of required retention force given a 21 mm valve area), the sutures exhibit approximately a 100:1 overcapacity in terms of retention force. Therefore, since physiologically the body cannot generate 100+ lbs of pulling force there must be some other reason for using all fifteen suture pairs. In fact, the only reason to use so many sutures is to compress the annulus tissue against the sewing ring around the entire annulus to create a leak free seal to the valve. It then follows that if one can provide the same amount of seal between the annulus and the cuff with fewer sutures, the mechanical pull-out or retention force requirements will still be met as well as the sealing requirement. Therefore, with the present invention, only 9–12 staple anchored suture pairs, or even less, will perform as effectively as the 15–18 suture pairs currently used. The reduction in suture pairs can alone shave approximately fifteen minutes off the procedure time, which is significant. In addition to the reduction of sutures placed, the inventive device will reduce the amount of time used to place the sutures in the annulus because there is no required exchange of needles from pushing the needle into the annulus to pulling the needle from above.

Another form of the staple includes suture attachment locations that are spaced apart from each other. This suture placement spreads out the force associated with the anchor over a larger area of the anchor thereby reducing the stress applied to the patient or to the prosthetic device.

Still another form of the staple permits the suture to run through the staple so a running suture can be used. In this manner, one suture can connect a plurality of staples and thus a minimum number of suture knots are needed. The running suture also permits the anchor elements to be pre-attached to the prosthetic device whereby the staples can be set, the prosthetic device moved along the sutures and into place and then the sutures tied off. This places the suture knots in a location that is easy to manipulate by the surgeon, and uses a minimum number of knots. This can substantially reduce surgical time.

As discussed above, since not all patients have the same sizes and spacings on the tissue that will support the prosthetic device, the present invention includes a means for permitting the surgeon to add fasteners to the suture. This means includes a running suture with loops that can have anchors attached thereto as necessary. If not all loops are used, the suture will be pulled taut in the cuff to delete the loop. On the other hand, if an anchor is to be added, it can be attached to a loop and when the suture is pulled taut, the anchor will act in the manner discussed herein for anchoring the suture to the tissue. A suitable anchor is disclosed which includes suture attaching elements as well as tissue attaching elements on a base.

BRIEF DESCRIPTION OF THE DRAWINGS

FIG. 7A is an exploded view of another form of the staple used in the present invention.

FIG. 7B is an assembled view of the staple shown in FIG. 7A.

FIG. 7C is a detail showing the attachment of the suture lead to the FIG. 7A–7B staple.

FIG. 7D shows another form of the staple of the present invention.

FIG. 12 is a further cross sectional view similar to that shown in FIGS. 10 and 11 illustrating a portion of the staple placement process.

FIG. 13 shows a needle grabber of the present invention in position to retrieve a needle during the placement process of the present invention.

FIG. 14 is an isometric view of the distal end of the instrument of the present invention.

FIG. 15 is a view taken along line 15—15 of FIG. 14 showing the tracks used to mount the needle grabber and the staple driver operator on the base of the tool.

FIG. 18 is a view of the cassette in an open condition.

FIGS. 19–22 show the preferred form of the tool used in placing staples and pulling suture leads according to the teaching of the present invention in various stages of carrying out the method of the present invention.

DETAILED DESCRIPTION OF THE PREFERRED EMBODIMENT OF THE INVENTION

Figure 1:
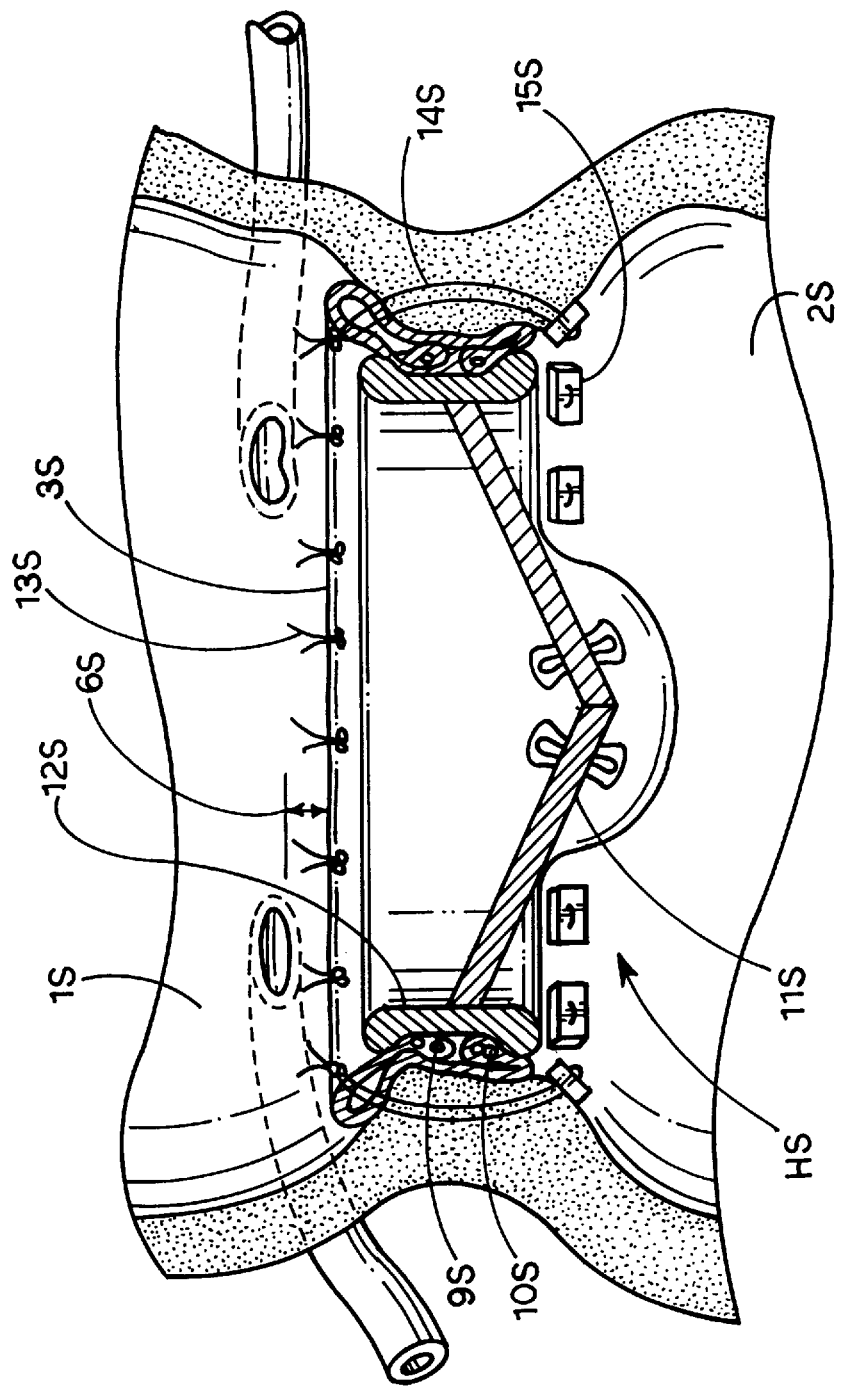
FIG. 1 shows a sectional view of a prior art prosthesis valve in place in a patient.

Since the preferred form of the fastener and tool of the present invention is used in connection with a heart valve, such use will be discussed herein. Referring first to FIG. 1, a prior art prosthetic heart valve HS is shown installed in the annulus of an aorta 1S next to a left ventricle 2S. Valve HS is secured in place by a series of sutures 14S which are tied in knots 13S. The sutures are most often used with felt pledget 15S to spread the load of the sutures evenly so as not to tear the tissue. Valve HS includes a cuff 3S which is attached to the perimeter of base 12S of valve HS in the factory. Drawstrings 9S and 10S are used to effect this attachment. The cuff and valve body are implanted as a single unit with the cuff being hand sewn to the tissue. Leaflets 11S are also shown as is the distance between the top plane of the valve and the right coronary artery junction with the aorta. This distance is indicated in FIG. 1 by numeral 6S.

Figure 2:
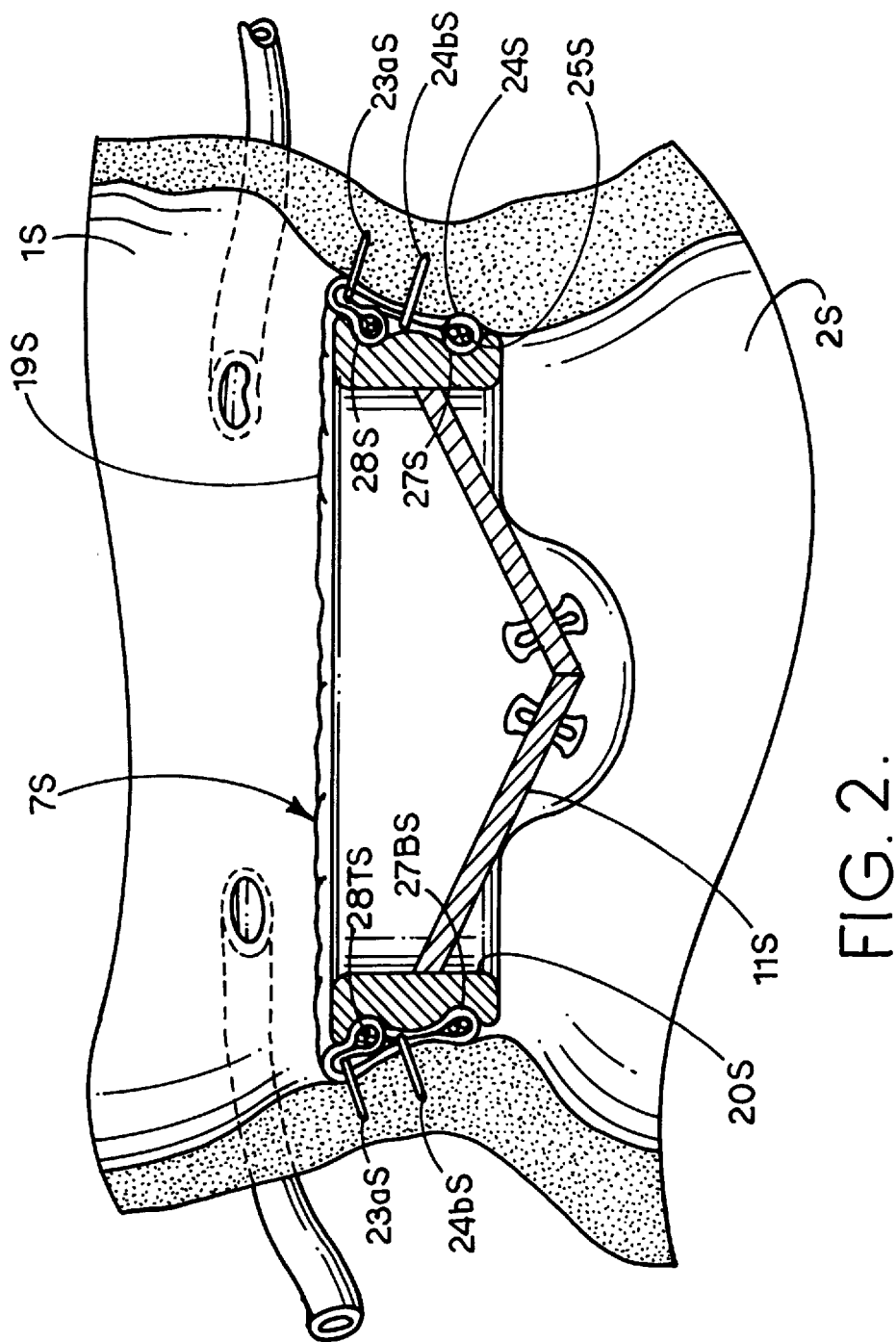
FIG. 2 is a sectional view of the prosthesis valve shown in the referenced patent application in the aortic annulus of a patient.

Shown in FIG. 2 is a prosthetic valve 7S embodying the invention disclosed in the referenced patent application installed and seated in the annulus of the aorta. Fasteners 23aS and 24bS are used to fasten sewing cuff 19S to the annulus of the aorta. The fasteners are staples in the preferred form of the invention. Drawstrings 27S and 28S are used to secure the cuff to the body 20S of the valve, and an indicating means 25S, such as a garter spring or the like, is located in the lower section of the cuff. One form of the indicating means includes a garter spring inside a pocket in the cuff. Indicating means 25S is used to signal the surgeon when the heart valve body 20S has been seated properly in the cuff 19S prior to activating the drawstrings. Contact between means 25S and the valve body provides the surgeon with a tactile signal that the valve body is properly seated in the in-situ cuff. FIGS. 1 and 2 are more fully discussed in the incorporated U.S. patent application Ser. No. 08/606,343, and attention is directed thereto for such further discussion if desired. The letter "S" has been added to all of the reference indicators in FIGS. 1 and 2 to identify the elements as being disclosed in the referenced patent application.

The intent of the suture anchor of the present invention is to provide a more secure anchor point for a suture pair. One requirement is that it must resist being pulled through the tissue. To facilitate this the staple shape has an enlarged base which spreads the load out on the surrounding tissue and provides a high pull out resistance. In addition, ears on the base provide adequate area to hold the staple in a driving tool while forming the staple.

Figure 3:
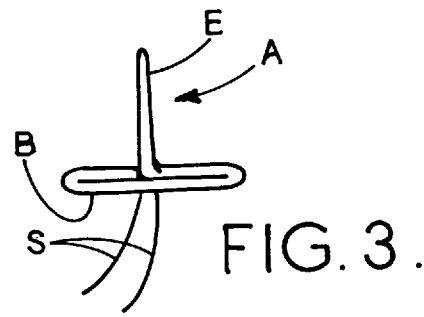
FIG. 3 shows a generic anchor element.
Figure 9:
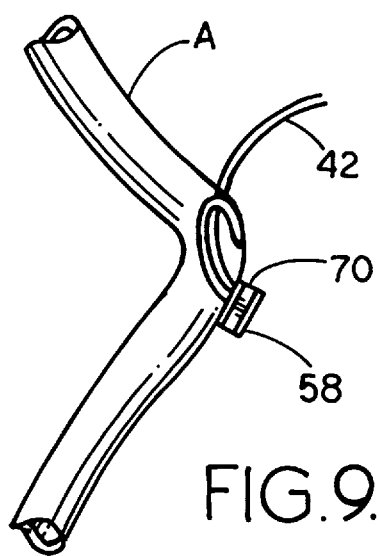
FIG. 9 is a view showing the staple of the present invention mounted on an aorta.

Shown in FIG. 3 is a broad illustration of the suture anchor of the present invention. As shown in FIG. 3, suture anchor A is one piece and includes an anchor base B which has at least one deformable element E attached thereto and a suture S attached thereto near the base of the deformable element. Base B is large in comparison to the transverse cross section of deformable element E and is located in abutting contact with a patient's tissue whereby forces exerted thereon by suture S are spread out over an area larger than a fastener head known to those skilled in the art. This spreading of forces prevents the anchor from being pulled through the tissue, even if the tissue is fragile. As used herein, the term staple will refer to the anchor, and the term prong will refer to the deformable element that is forced through a patient's tissue and which is deformed to hold the anchor in place on the tissue with base B abutting the tissue. The suture has suture needles on the ends and these needles are positioned on base B to be forced through the tissue when the deformable elements are forced through the tissue. As can be understood from the teaching of this disclosure, since the suture is attached to base B, forcing the suture needles through the tissue places the tissue between the needles and the base B so the base acts as an anchor for the suture. Pulling force on the sutures is then spread out over the area of the base. The deformable element is bent over in the manner of a staple after passing through the tissue twice as will be discussed below to firmly fix the anchor to the tissue. Passing through the tissue twice permits the anvil used to deform the deformable element to be located outside the tissue, i.e. on the same side of the tissue as the in-place anchor base. It is noted that the suture also passes through the tissue twice so the element used to grasp the suture needle can be located on the same side of the tissue as the in-place anchor base. This is best illustrated in FIG. 9.

Figure 3A:
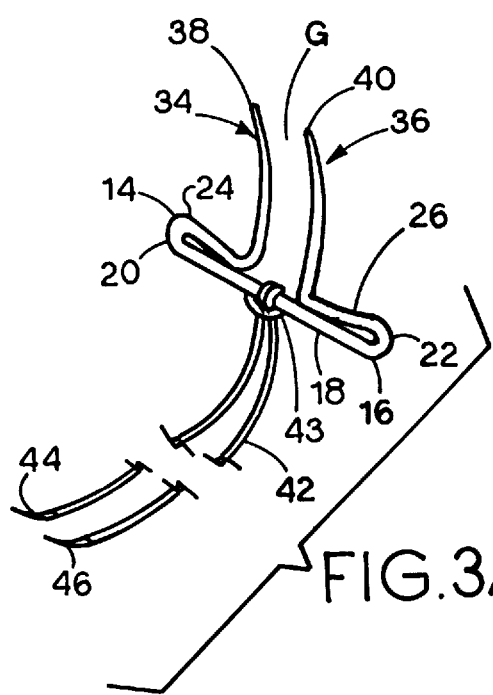
FIGS. 3A–3C show a first form of the staple embodying the present invention.
Figure 3B:
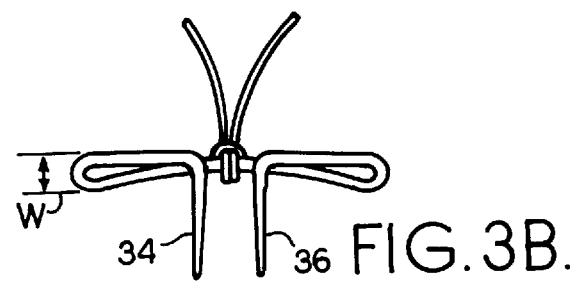
Figure 3C:
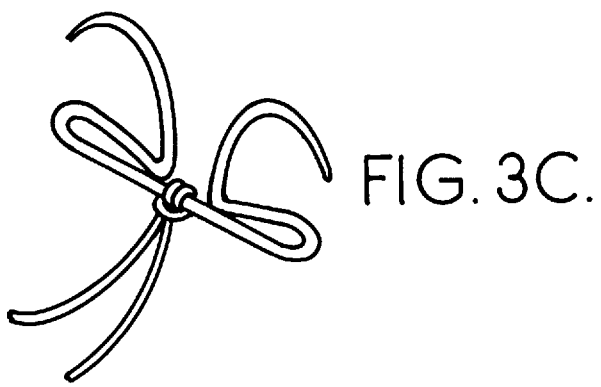

Shown in FIGS. 3A, 3B and 3C is a first form of the staple of the present invention. As shown in FIG. 3A, a staple 10 includes a base 12 having ends 14 and 16 and a central section 18. First bends 20 and 22 are reverse bends and are located on each end 14 and 16 respectively, and return sections 24 and 26 extend toward each other and each extends towards the other end for some length of the base central section 18. The first bends change direction 180° in the manner of a hairpin. Second bends 30 and 32 are located on inner ends of the sections 24 and 26 respectively and change direction 90°. Prong elements 34 and 36 extend from the bends 30 and 32 respectively to have a proximal end at the bend 30, 32, and a distal end 38, 40 spaced from the central section 18. As shown in FIG. 1A, the staple 10 is a one-piece construction. That is, the staple 10 is a monolithic element formed of one piece of material.

The prong elements 34 and 36 are spaced apart along the length dimension of the base 12 to define a gap G therebetween. A suture lead 42 is tied in a knot 43 to the base central section 18 between the prong elements, and needles 44 and 46 are attached to lead 42. FIG. 3B shows a to plan view of staple 10 and illustrates that prongs 34 and 36 are slightly offset from base 12. As is also shown in FIG. 3B, base 12 is arcuate. The curved form of the base permits the base to match the curvature of the aorta.

FIG. 3C shows staple 10 in a crimped configuration. Prong distal ends 38 and 40 have been bent over to penetrate tissue as will be understood from the following discussion.

Figure 4A:
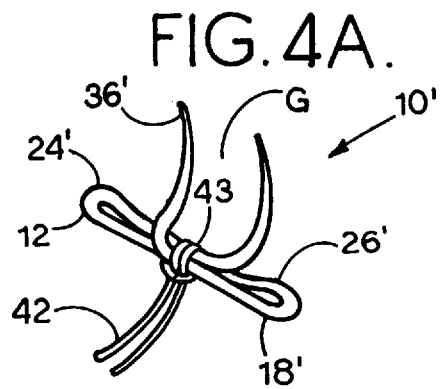
FIGS. 4A and 4B show a second form of the staple of the present invention.
Figure 4B:
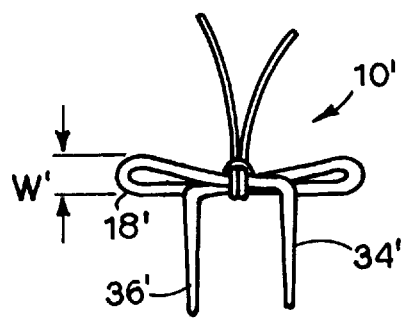

Shown in FIGS. 4A and 4B is a staple 10' which is similar to staple 10 except the sections 24' and 26' extend past each other and cross each other near the midpoint of base 12 so that prong elements 34' and 36' are on opposite sides of the base from prong elements 34 and 36 of staple 10. Suture lead 42 is wrapped around the extended sections 24' and 26' as well as around base 12. Base 12' is also curved as was discussed above in connection with base 12. The overlapping of the sections 24' and 26' creates a wider base. That is the width dimension of staple 10' is greater than the width dimension of staple 10, with the width dimension being indicated in FIGS. 3B and 4B as dimension W.

Figure 5A:
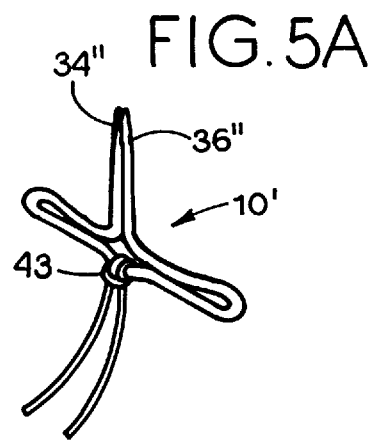
FIGS. 5A–5C show yet another form of the staple of the present invention.
Figure 5B:
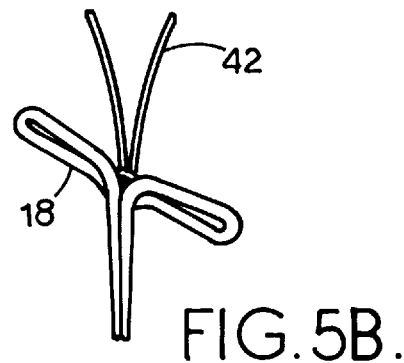
Figure 5C:
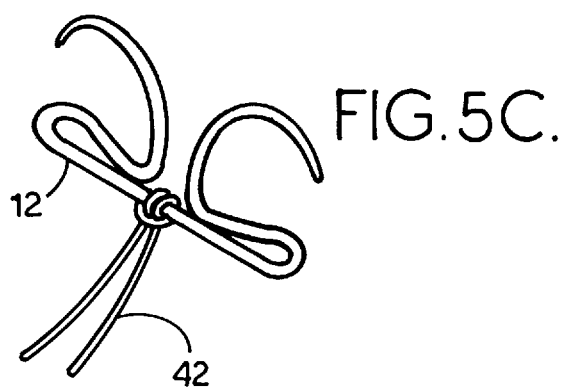
Figure 6A:
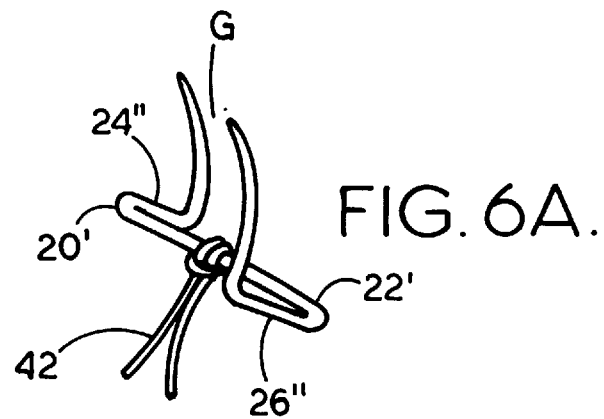
FIGS. 6A–6C show another form of the staple of the present invention.
Figure 6B:
Figure 6C:
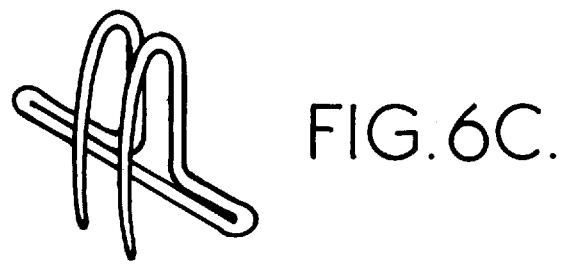

Staple 10" shown in FIGS. 5A–5C, is similar to staple 10 except that prongs 34" and 36" are in abutting contact with each other. This causes the staple to make an incision hole that is smaller than that made by staple 10. FIG. 5C shows the prong elements in their crimped configuration, with FIG. 5B showing the top plan view and width dimension of the staple and the curved nature of the base thereof as discussed above.

Staple 10'" shown in FIGS. 6A–6D is similar to staple 10 except that bends 20' and 22' are rotated 90° from the plane containing those bends for staple 10. Base 12 is located between the sections 24" and 26" attached to bends 20' and 22'.

Staple 10"" shown in FIGS. 7A and 7B is fabricated from flat metal stock. Staple 10"" includes a stamped metal base 18'" having ends 50 and 52 separated from each other along the length dimension of the base, sides 54 and 56 separated from each other along the width dimension of the base, and tissue engaging surface 58. Base sides 54 and 56 are curved to match the curvature of the aorta, and side 54 includes a plurality of tool docking notches 58 to facilitate the alignment and gripping of the driver to the fastener. In this manner, slippage is minimized and alignment between the fastener and the driver is insured. Two suture lead accommodating holes 60 are defined in base 18'" to receive suture lead 42 to anchor that lead to the base as discussed above in regard to staple 10.

Two prongs 62 and 64 extend from proximal ends thereof away from base 18'" to have distal end points 66 and 68 respectively located in spaced relation to each other and to base 18'". While not shown, a single prong can be used in place of the two prongs shown in FIGS. 7A and 7B. The suture lead is looped through the holes 60 as shown in FIG. 7C to attach the suture lead to the base by a knot 61. A felt pad 70 can be placed on top of surface 58 to protect fragile tissue from the forces associated with the staple. This is especially useful in older patients. A preferred material for pad 70 is PTFE, similar to that used on existing heart valve sutures. FIG. 7D shows the staple IV and the suture lead 42 looping through the holes 60 of the base.

It may be advantageous to shape base 18'" to allow for features that cannot be obtained with the wire staple 10. For instance, it will be easier to regulate the overall width of the base to more effectively spread the load. In addition, a special narrowing can be designed along with the width of the staple or prong legs and they can be customized to provide specific weak pints to allow the bend or fold to be located in one area. The tool engaging notches 58 facilitate grabbing the fastener with a staple forming tool. Additionally, suture holes 60 allow for a better and more secure placement of sutures.

Figure 8:
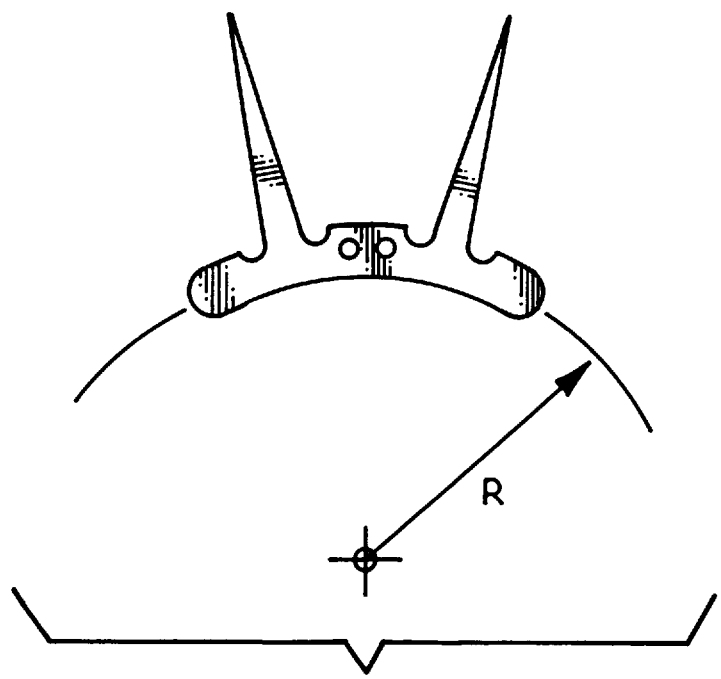
FIG. 8 is a top plan view of the FIG. 7 staple in flat pattern form.

FIG. 8 is a top plan view of fastener 10''' showing the curvature of the base 18''' whereby the base has an arc or curvature matching the curve of the aorta.

An in-place fastener 10'''' is shown in FIG. 9 with an aorta being indicated at reference indicator A. It is observed that the in place fastener 10'''' is very similar in appearance to an in-place fastener 10. A felt pad 70 is shown in FIG. 9 next to the tissue.

Figure 10:
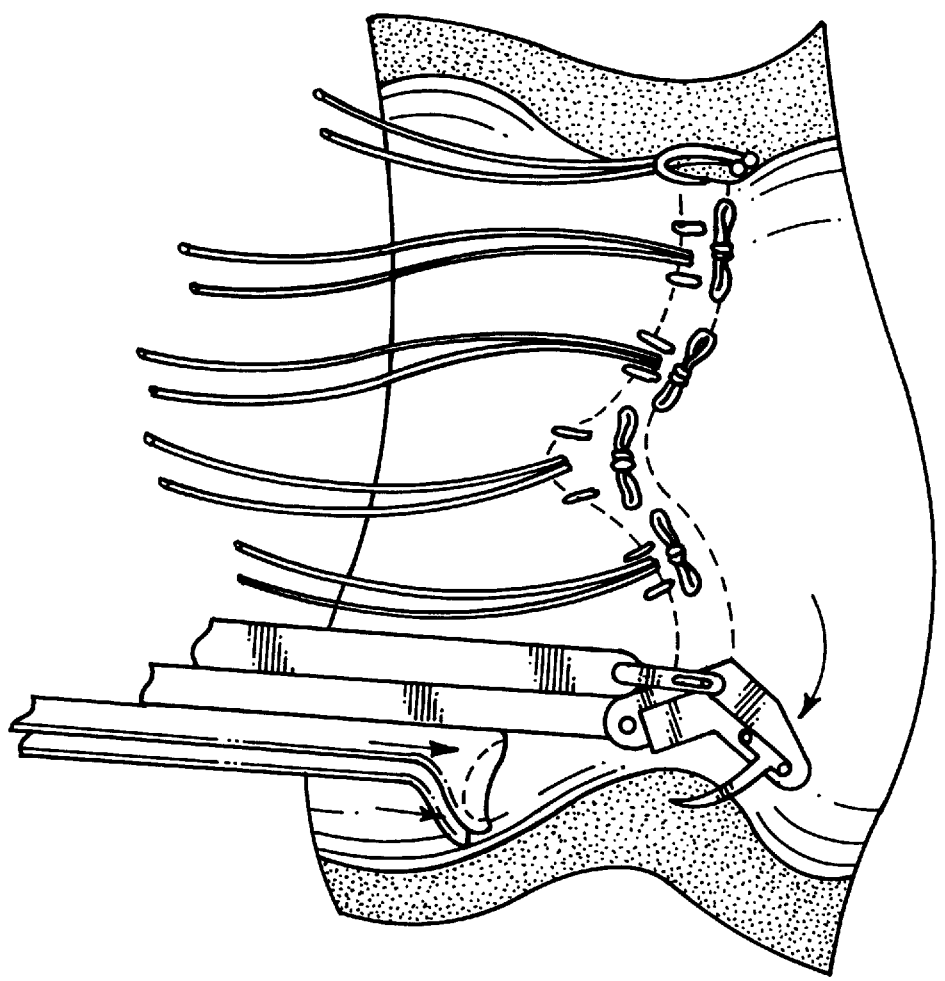
FIG. 10 is a cross sectional view through the aortic annulus showing five suture anchors placed in accordance with the teaching of this invention.

Shown in FIG. 10 is a cross-sectional view through an aortic annulus showing five suture fasteners or anchors that have been placed along the annulus of the aorta. Staple a is shown n the sectional view, crimped. Staples b, c, d and e are shown in plan view with the sutures extending upwardly out of the aorta and the staple legs being crimped in place along the annulus. In the left portion of the figure, a section view is shown through an instrument T which shows how the staple is first inserted into the annulus coming from below the annulus, traveling through the tissue heading up toward the top of the annulus whereby the staple will be engaged by an anvil on tool T for crimping. A surgeon can also pull up on tool T to help pull the fastener through the tissue to assist tissue penetration. Tool T will be further discussed below.

Figure 11:
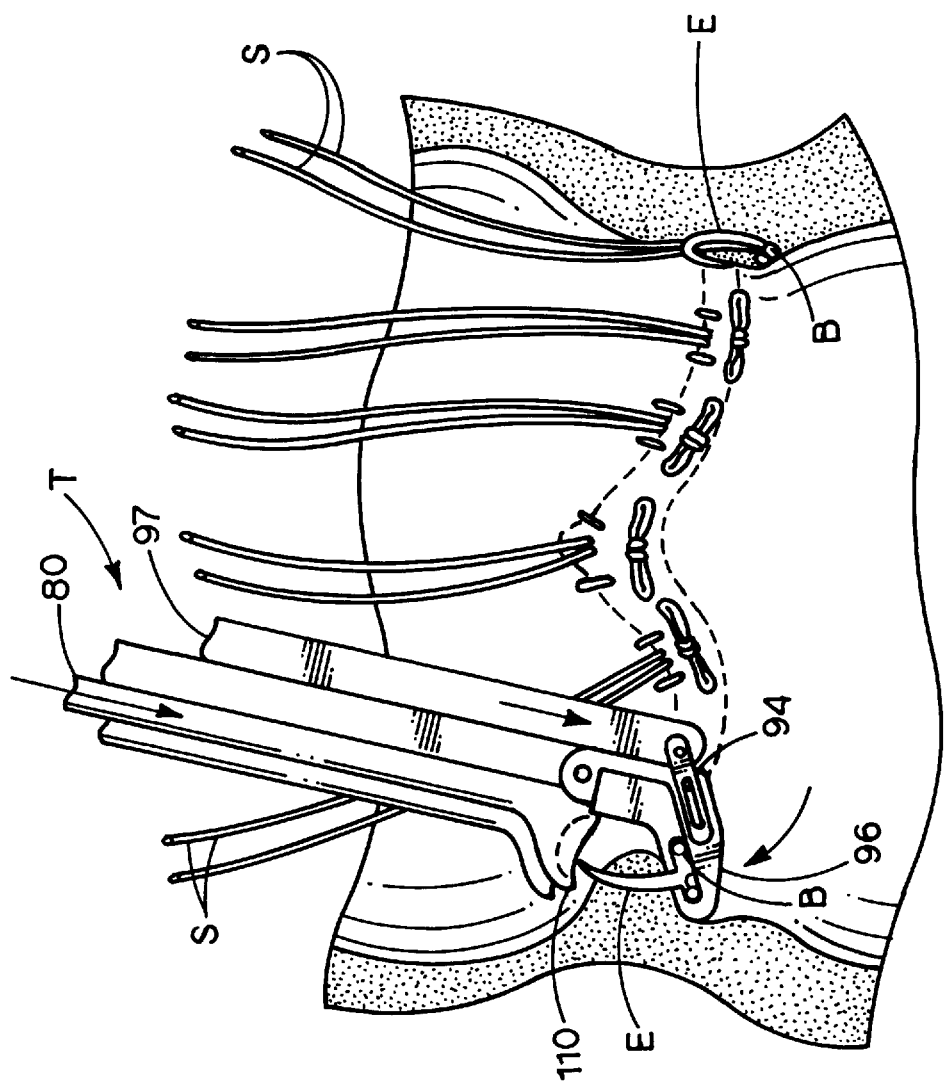
FIG. 11 is a further cross sectional view similar to that shown in FIG. 10 illustrating a portion of the staple placement process.

FIG. 11 shows the tool T rotating the staple through the tissue thereby bringing it into alignment with the anvil on the tool T. After rotation, the tips of the staple are in position against the anvil to crimp the staple after the staple has been driven through the tissue (twice, once into the tissue and once out of the tissue). FIGS. 12 and 13 shows the tool having a needle grabber grabbing a needle to release it from a cassette and retain it to pull the suture lead out of the patient.

Tool T is shown in FIGS. 14, 15 and 19–22. As shown in FIG. 19, tool T includes a base 80 having a proximal end 82, a distal end 84 and a longitudinal centerline CL. An operating mechanism 86 is located on proximal end and will be located outside of the patient and includes a housing 88 and a handle 90. Handle 90 is pivotally mounted on housing 88 which is mounted on base 80. Handle 90 moves in direction 92 to operate the tool to drive a staple through tissue and from the staple.

A fastener deployment mechanism 94 is located on distal end 84 and includes a drive link 95 connected at one end thereof to a driver saddle 96 and at the other end to a rotator rod 97 that operatively connects the link 94 to handle 90 of the operator mechanism. In this manner, the fastener storage and deploying mechanism is operatively connected to the operating mechanism.

A needle gripper 100 is slidably mounted on the base to be located adjacent to distal end 84 and moves in direction 102 in response to corresponding movement of hand grip element 104 due to an operative connection therebetween. A rod 106 operatively connects needle gripper 100 to hand grip element 104.

At least one anvil 110 is mounted on distal end 84 adjacent to driver saddle 96 for a purpose that will be understood from the following discussion. A spring 112 is connected at one end thereof to housing 88 and at the other end thereof to handle 90 to control movement of that handle. Rotator 97 is also connected to handle 90 to move in direction 92' when handle 90 is moved in direction 92.

Figure 16:
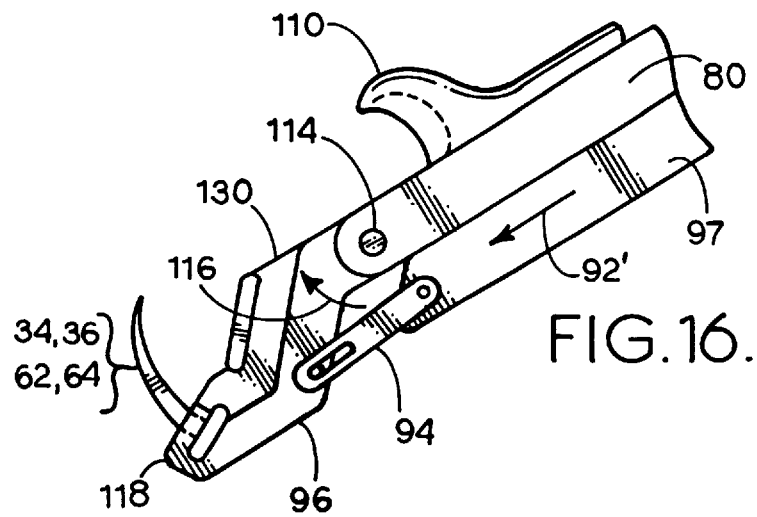
FIG. 16 illustrates the distal end of the tool with a staple positioned thereon.

As shown in FIG. 16, driver saddle 96 is pivotally attached to base 80 by a pivot pin 114. Driver link 94 is pivotally connected at one end thereof to rotator 97 and pivotally connected to driver saddle 96 at the other end thereof to move driver saddle 96 in direction 116 in response to rotator movement in direction 92'. Saddle movement in direction 116 moves distal end 118 of the saddle upwards and toward anvil 110. A fastener prong 34, 36, 62, 64 will thus be driven upwardly and backwards toward anvil 110 by fastener movement and/or by anvil movement or by a combination of both. Contact between the fastener prong and the anvil forms the fastener prong. The anvil is curved to smoothly accomplish this forming as will be understood by those skilled in the art.

Referring to FIGS. 14 and 15, it can be seen that there are two anvils 110 to correspond to the two prongs of the fastener. Each anvil is mounted in tracks 120 defined in base 80 and needle gripper 100 is mounted in track 122 defined between the anvils. Needle gripper 100 slides with respect to base 80 and rotator 97 is also slidably anchored to base 80 by a track 124 engaging projections 126 of the rotator. Corresponding projections are located on the anvils and on the needle gripper to slidably mount those elements in the corresponding tracks as will be understood by those skilled in the art. A suitable needle gripping material 103 such as urethane or thermoplastic elastomer is located in the needle gripper 100 to grab the needle and hold that needle while the needle is being pulled out of the patient by the needle gripper. Element 106 operatively connects handle 104 to the needle gripper 100 to move that gripper as necessary to engage the points of the suture needles with sufficient force to capture those needles securely enough so the needles can be removed from the patient when the tool is withdrawn.

Figure 17:
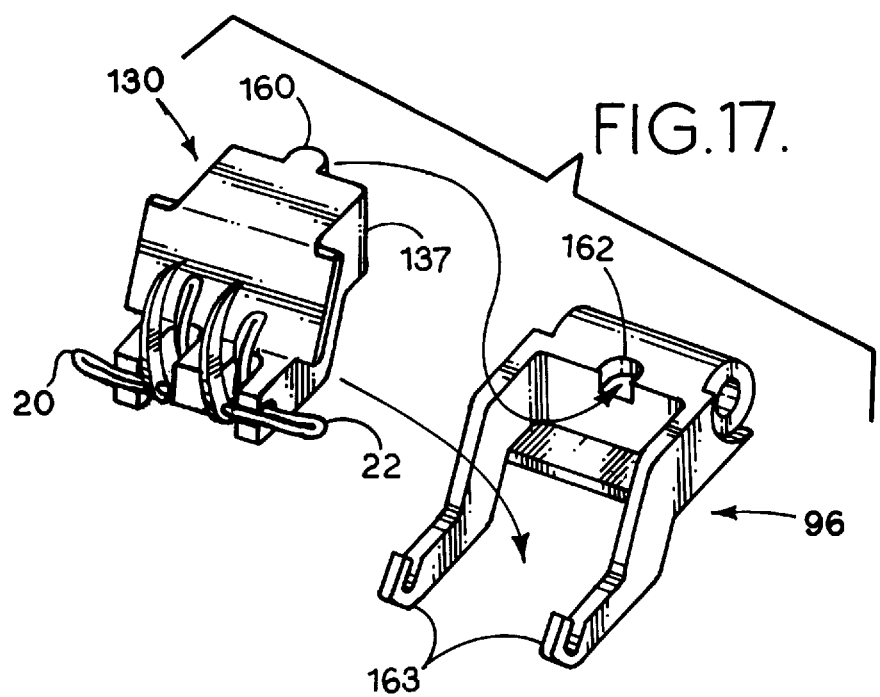
FIG. 17 is an exploded view of the distal end of the tool with a cassette illustrating the relationship of the cassette to the tool.

A cassette 130 is shown in FIGS. 17 and 18. Cassette 130 is releasably mounted on driver saddle 96 as indicated in FIG. 17 to mount the staples and sutures in operative position. As shown, cassette 130 includes an Z-shaped housing 132 having a long leg 134 connecting two short legs 136 and 137 together. Housing 132 is hollow and has a suture storage compartment 138 defined therein. A cover 140 is hingeably connected to housing short leg 137 to cover compartment 138 for maintaining a suture lead 42 in that compartment. Short leg 136 includes two hook-shaped lugs 142 and 144 that releasably engage fastener base 12 of the staple or suture anchor, such as staple 10, adjacent to the first bends, such as 20 and 22 to hold the fastener in place on the cassette. A suture needle retention mount 150 is located on short leg 136 between lugs 142 and 144 and releasably mounts a suture needle, such as needle 44, 46, in place on the housing. A suture lead hole 152 connects the outside of the cassette to the compartment 138 whereby suture lead 42 can extend through the housing into the compartment to be stored therein while being connected to sutures mounted in mount 150.

Cassette 130 is releaseably mounted on saddle 96 as indicated in FIGS. 16 and 17. A lug 160 on housing short leg 137 fits into a lug accommodating slot 162 defined on saddle 96. The sliding fit between lug 160 and slot 162 in combination with the releasable fit between the staple base and lugs 142 and 144 combine to releasably hold cassette 130 in position on driver saddle 96 as indicated in FIG. 16. When the cassette is in the FIG. 16 position, the prongs of the staple and the suture needle are in position to be set into a patient. Furthermore, when the cassette is in position on the saddle, the outer ends of the staple base, adjacent to bends 20 and 22, engage hooks 163 on the saddle 96 to be releasably held in the desired position and orientation during positioning and forming. Once the staple is placed and formed and the suture needle is grabbed and pulled up out of the cavity, the tool is twisted to release the staple base from hooks 163 and from lugs 142 and 144 to permit the fastener anchor to remain in place when the tool is removed from the patient. The needles are removed from the gripper and set aside for other uses. The cassette is disposable and is thus discarded. A new loaded cassette is then placed on the tool. The process is repeated as often as necessary to carry out the procedure. One fastener anchor is placed for each insertion of the tool.

The operation of the above-described system is indicated in FIGS. 19–22.

A sectional view of the tool is shown in FIG. 19. As shown in FIG. 19, base 80 is rigidly attached to housing 88, with the housing 88 containing the pivoted handle mechanism. The handle is, in turn, pivotally connected to both the rotator 97 and to the anvils 110 so that a single motion of the handle will in turn first rotate the driver saddle 96 about the pivot axis perpendicular to the centerline CL defined by pin 114 in direction 116 and secondly crimp the staple. The anvil can be slidably mounted on the tool so movement of the rotator will cause the anvil to slide forward into a prong crimping location. This single motion can be actuated in two separate motions to gain a stepwise control of the device. In addition, the needle gripper 100 is actuated in a longitudinal direction as indicated by arrow 102. Operation of the needle gripper can be independent of the movement of handle 90. The needle gripper grabs the needles 44, 46 and withdraws them in order to pay out the suture lead from the cassette. Movement of the needle grabber in a direction opposite to direction 102 by corresponding movement of handle 104 draws the suture needle through the patient's tissue as the staple prongs are being crimped due to their forced contact with the anvils 110.

FIG. 20 shows the first portion of this procedure wherein the rotator has moved longitudinally in a distal direction 102 to rotate the driver and in turn the handle moves further and crimps the staple in the tissue after the staple prongs have been forced through the tissue.

FIG. 21 shows the staple in a crimped configuration. After crimping the staple, the gripper handle is moved longitudinally in a distal direction to engage the tip of the suture needle into the soft gripper material 103. This drives the needle tip into material 103 and retains the needle tip in that material. The needle can be removed when desired.

Figure 22:
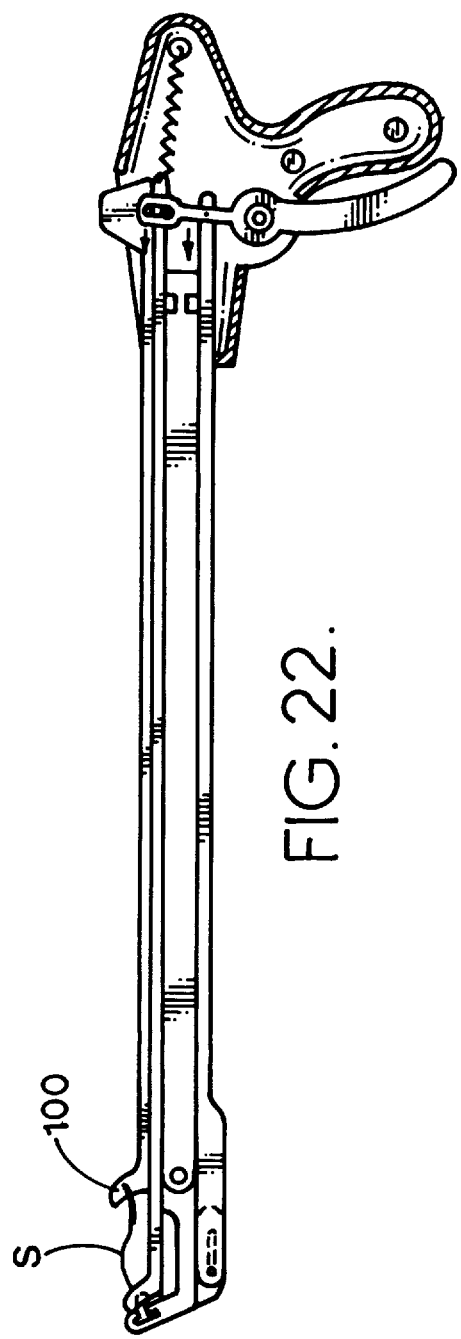
Figure 23:
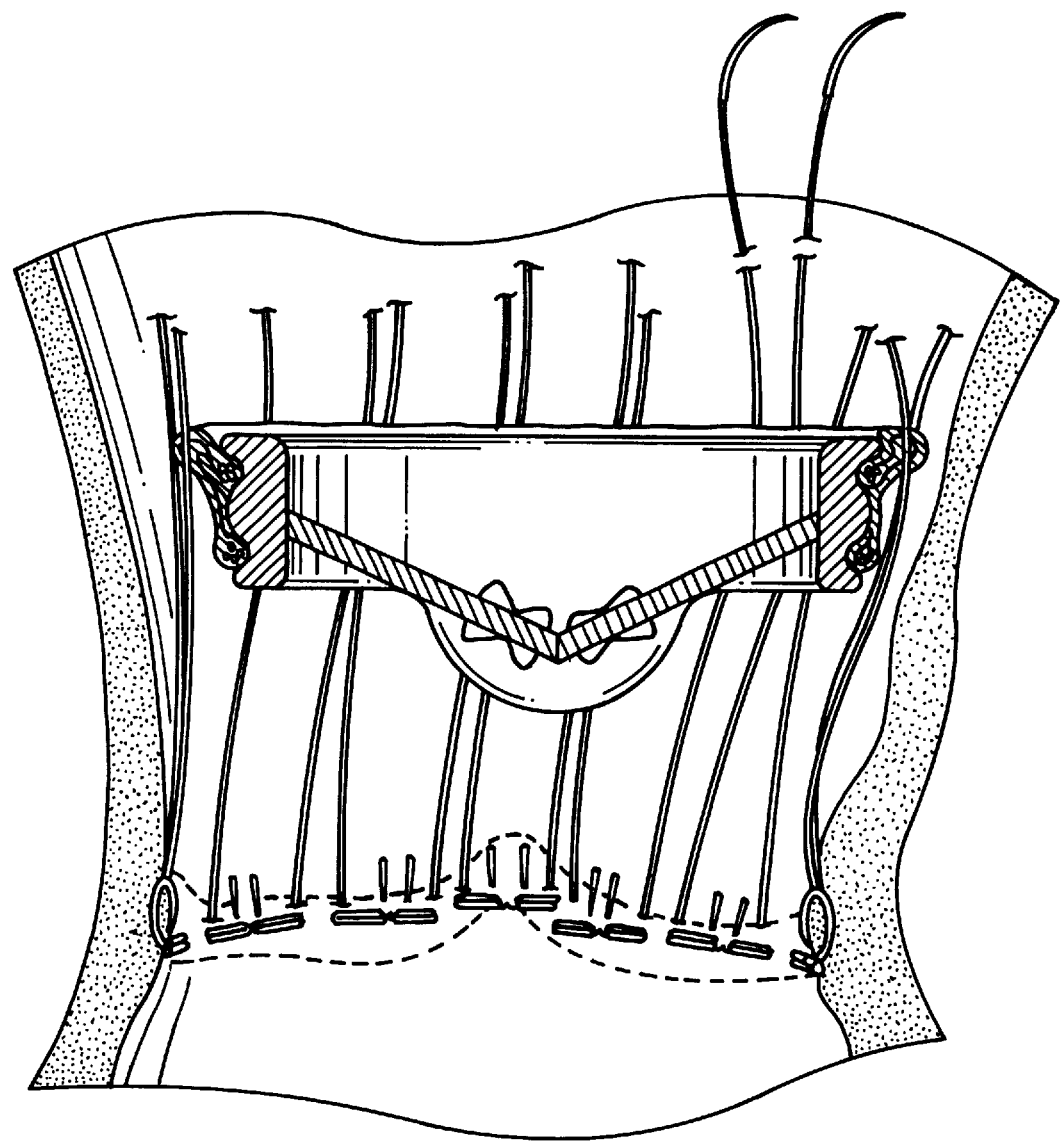
FIG. 23 shows a sectional view of a valve being slid down sutures to seat in an aorta.
Figure 24:
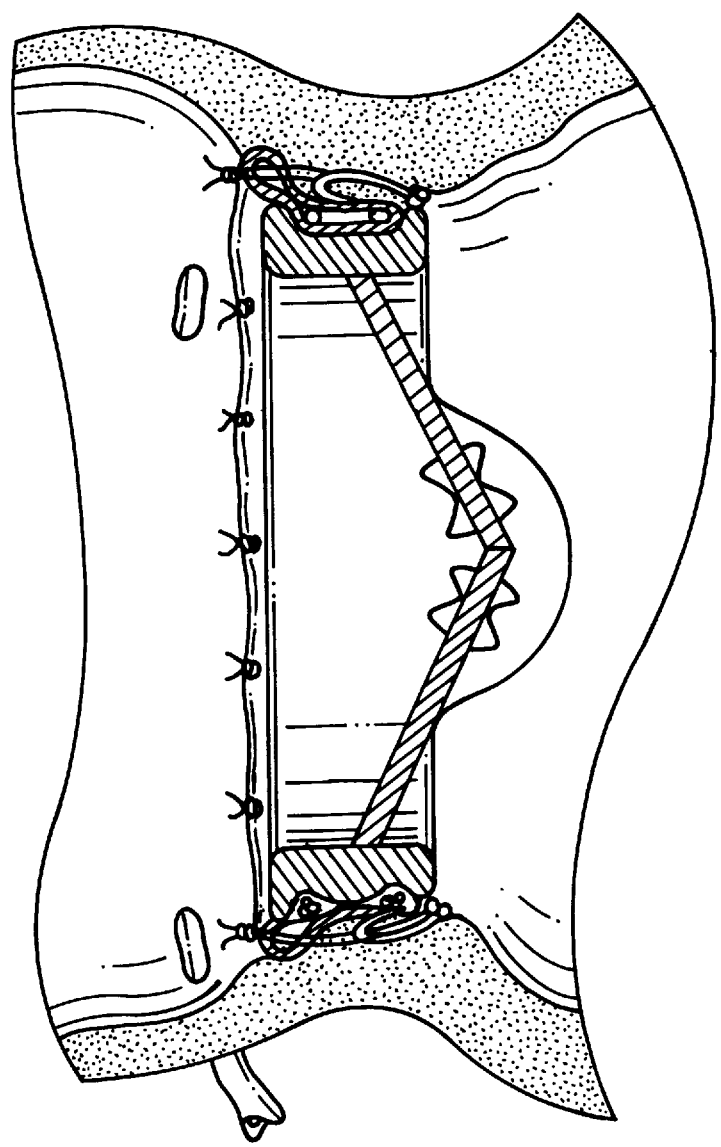
FIG. 24 is a sectional view of the valve installed and tied off in the aorta.

In FIG. 22, the grabber handle is pulled back which draws the needle out of the cassette and allows the suture lead to follow paying out the suture through the tissue. The handle 88 is then manipulated so that driver saddle 96 is disengaged from the staple. The tool T is then removed from the patient's body. Since the suture needle is still attached to the needle grabber, and the suture lead is still attached to the staple, such tool movement will withdraw the suture needle from the patient thereby providing access to the suture lead. Once the suture lead is located outside the patient, the old cassette is removed from the tool, and a new cassette is placed on the driver saddle 96. The tool is inserted back into the patient, and the process is repeated. The process is repeated until all of the sutures and staples are placed around the annulus. The sutures are then placed into a prosthesis, such as a heart valve sewing cuff (see the disclosure in the referenced patent application). The prosthesis is then guided into place as indicated in FIG. 23 and the operation completed when the valve is installed and tied off in the aorta as shown in FIG. 24.

Figure 25:
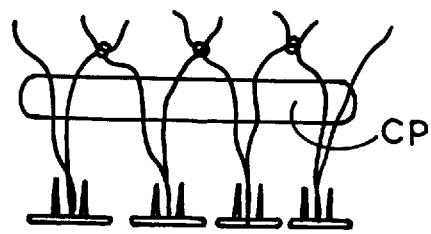
FIG. 25 shows a suture tieing pattern in which sutures from adjacent anchors are tied together.

Referring to FIG. 3, it can be observed that suture S is attached to anchor base B near the center of that base. A suturing pattern using anchor A is illustrated in FIG. 25. As shown in FIG. 25, sutures from adjacent anchors are tied together, see sutures $S_1$ and $S_2$ from anchors $A_1$ and $A_2$. This pattern works well; however, it may not be totally desirable since some stress is placed on tissue or on the prosthetic device spanning the gap between anchors. The gap-located tissue or prosthetic device may be subjected to shear stresses in some instances.

Figure 26:
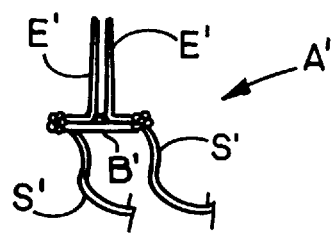
FIG. 26 shows an alternative form of anchor in which sutures are attached to the anchor at locations that are spaced apart from each other.

An alternative form of the suture anchor of the present invention is shown in FIG. 26 at A' which includes a base B' having at least one deformable element E' attached thereto. As shown in FIG. 26, two deformable elements E' and E" are included in suture anchor A'. Anchor A' differs from anchor A by having two sutures S' attached thereto at spaced apart locations. Anchor A' has sutures S' attached adjacent to each end thereof; however, other spaced apart locations can be used without departing from the scope of the present disclosure.

Figure 27:
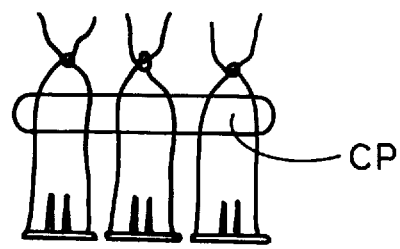
FIG. 27 shows a suture tieing pattern using anchors that have sutures attached thereto at spaced apart locations whereby sutures from one anchor can be tied together.

The spaced apart placement of sutures S' permits formation of a suturing pattern such as shown in FIG. 27. Sutures on each anchor can be tied together. Thus, in the FIG. 27 pattern each anchor can be considered separate from other anchors. Still further, the area of compression associated with a knot, indicated in FIGS. 25 and 27 at CP, is changed from between adjacent anchors in FIG. 25 to adjacent a single anchor in FIG. 27. The anchor base thus fully supports area of compression CP from anchor A'; whereas, the area of compression spans adjacent anchors in FIG. 25 for anchor A. Forces associated with the anchors are thus spread out over more desirable areas thereby reducing the stress placed on either the patient's tissue or on the prosthetic device itself.

Figure 28:
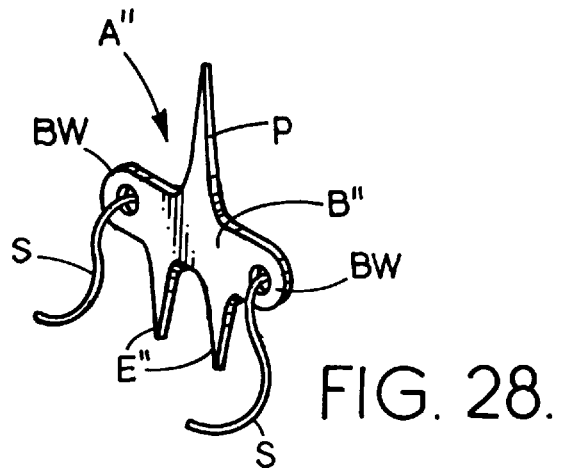
FIG. 28 shows another alternative form of anchor in which the anchor is one piece and monolithic.
Figure 29:
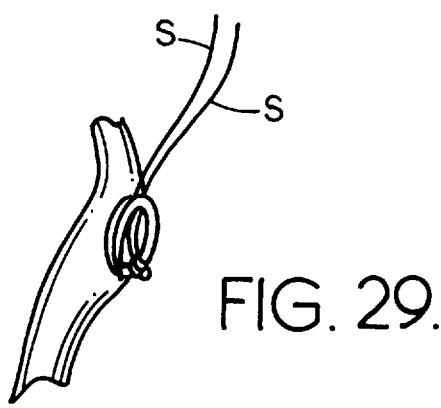
FIG. 29 shows the FIG. 28 staple in place.
Figure 30:
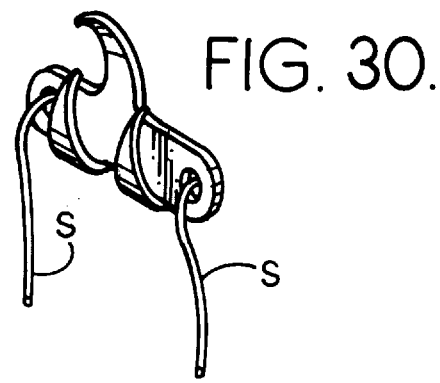
FIG. 30 shows the FIG. 28 staple in a deformed configuration.

Yet another form of suture anchor A" is shown in FIGS. 28–30. Anchor A" is one-piece and has a base section B" having two wings BW to which sutures S are anchored. Deformable elements E" extend from one side of base B" and security pin P extends from another side of the base. Elements E" are deformed after passing through the tissue and the anchoring portion of a prosthetic device to anchor the base to the patient's tissue and to the prosthetic device anchoring portion. Security pin P is also deformed to spread the load bearing portion of the anchor base to a larger tissue bite. The need for this will be understood by one skilled in the art based on the teaching of the present disclosure.

Figure 31:
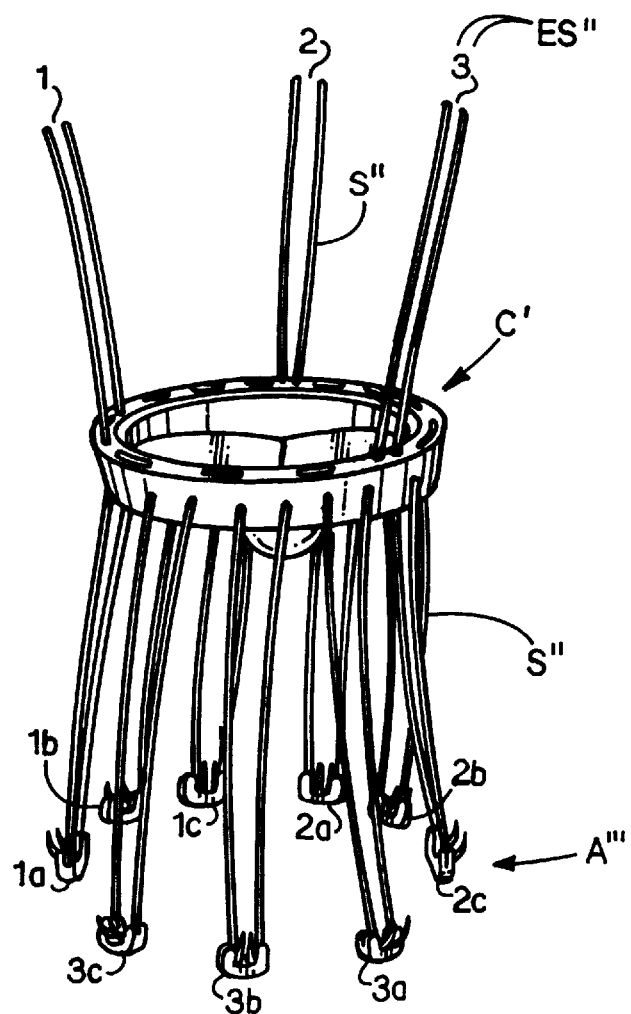
FIG. 31 shows an elevational view of the running suture prosthetic device.
Figure 34:
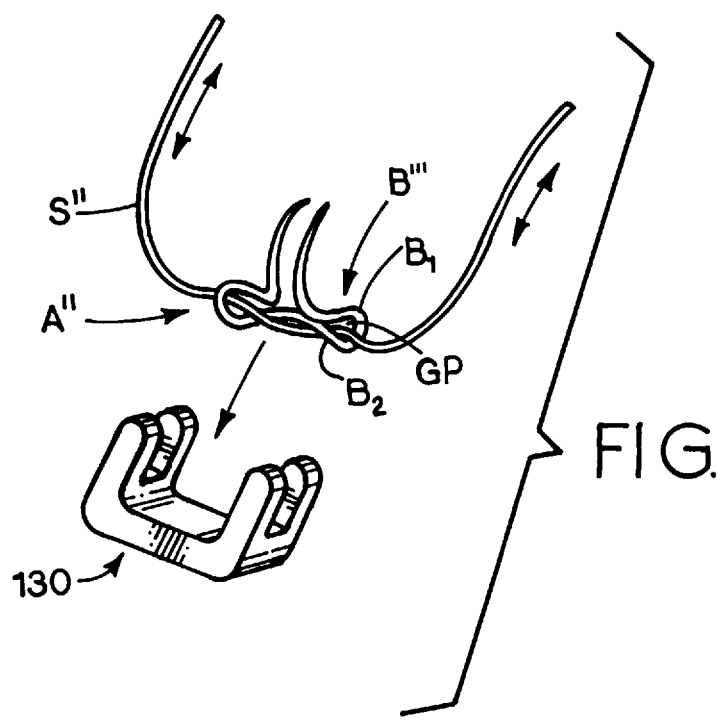
FIG. 34 shows an anchor with a running suture in combination with a cassette used to hold the anchor during placement.

Yet another form of suture anchor A''' is shown in FIGS. 31 and 34. Anchor A''' accommodates a running suture S" by having a base B''' with sections $B_1$ and $B_2$ that are spaced apart to define a gap GP therebetween. Suture S" is threaded about section $B_2$ and passes through gap GP to be attached to anchor A'''.

Figure 32:
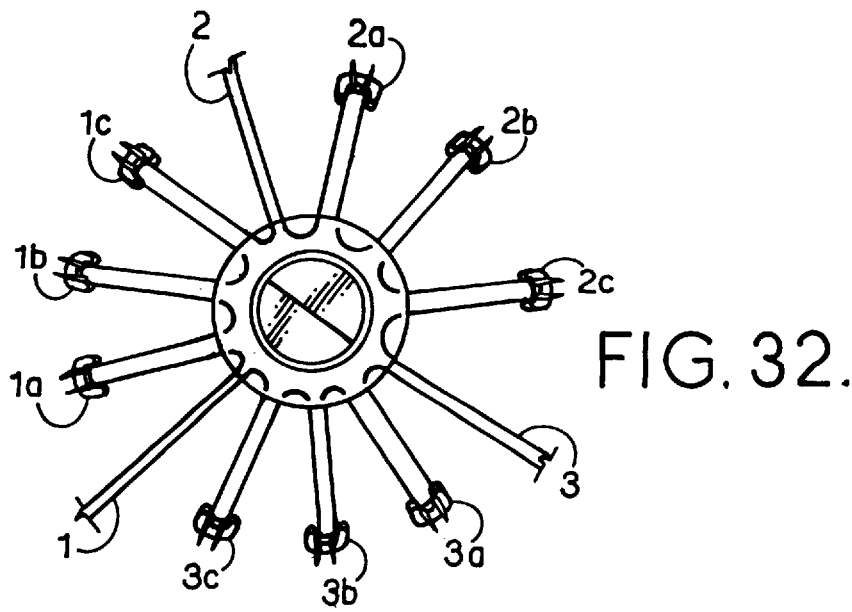
FIG. 32 is a top view of a prosthetic device having a running suture associated with anchors for that device.
Figure 33:
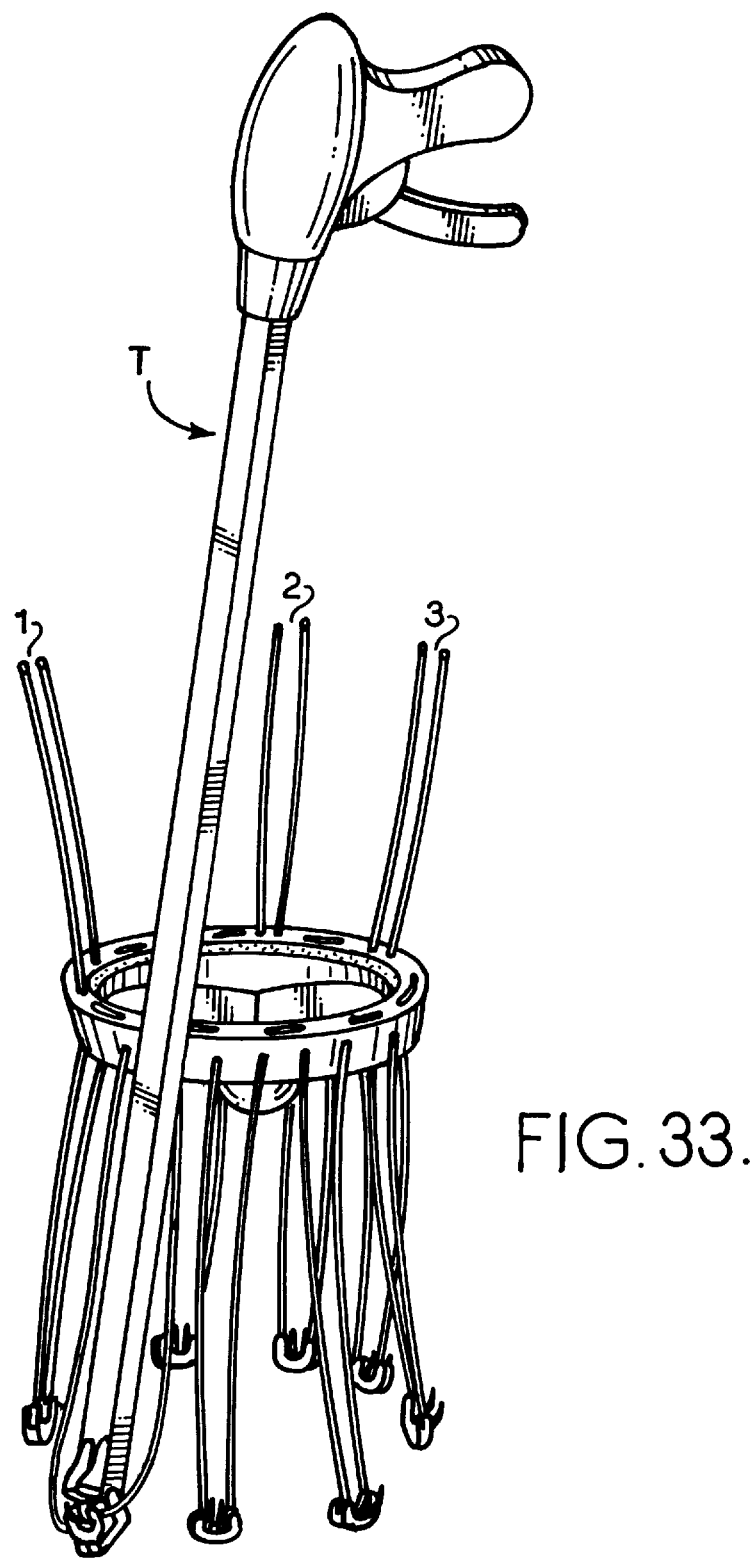
FIG. 33 shows a tool placing an anchor associated with the running suture prosthetic device.

A running suture can be used with a cuff C' shown in FIGS. 31 and 32. Cuff C' has anchors A''' pre-attached thereto by running suture S". As can be seen in FIGS. 31 and 32, suture S" extends from the anchors through the cuff and out of the cuff to ends ES" located outside a patient. Each anchor A''' is individually placed in the patient using a tool T such as described above, see also FIGS. 33 and 34 which show an anchor A''' in a cassette 130 which is mounted on a tool T as described above in regard to FIGS. 17 and 18. Then, the cuff is moved down over the suture into the desired position. Then, the suture is operated to draw the cuff tightly into place, and the suture is appropriately knotted and cut.

Figure 35:
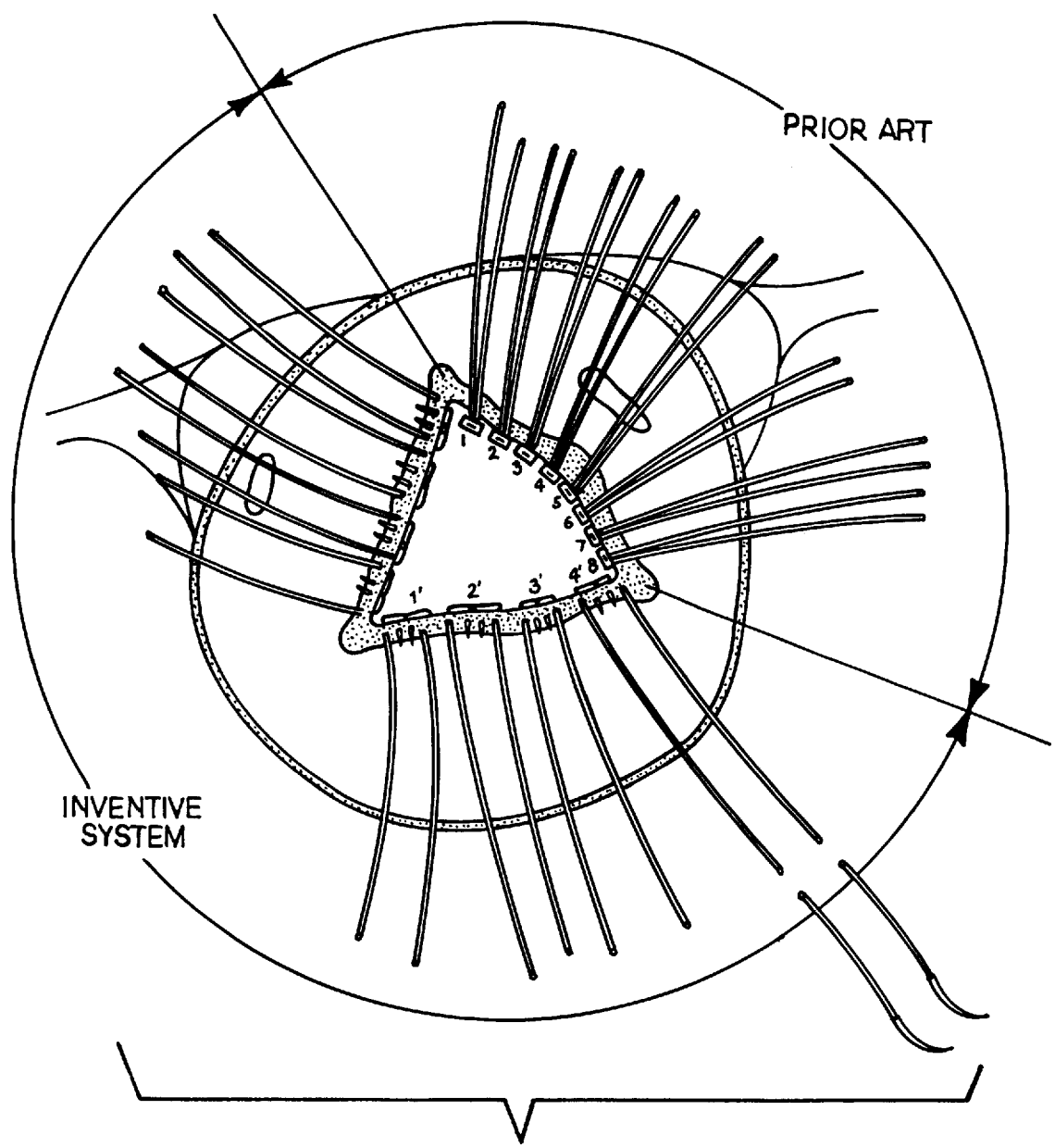
FIG. 35 is a comparison between the running suture device of the present invention and the prior art.

Only three suture elements need to be operated to set cuff C'. The improvement of the present invention over the prior art is illustrated in FIG. 35 where a multiplicity of sutures is replaced by a few suture elements of few running sutures. The running suture also provides improved visibility to the surgeon by locating the suture portions that must be manipulated in a convenient location.

Figure 36:
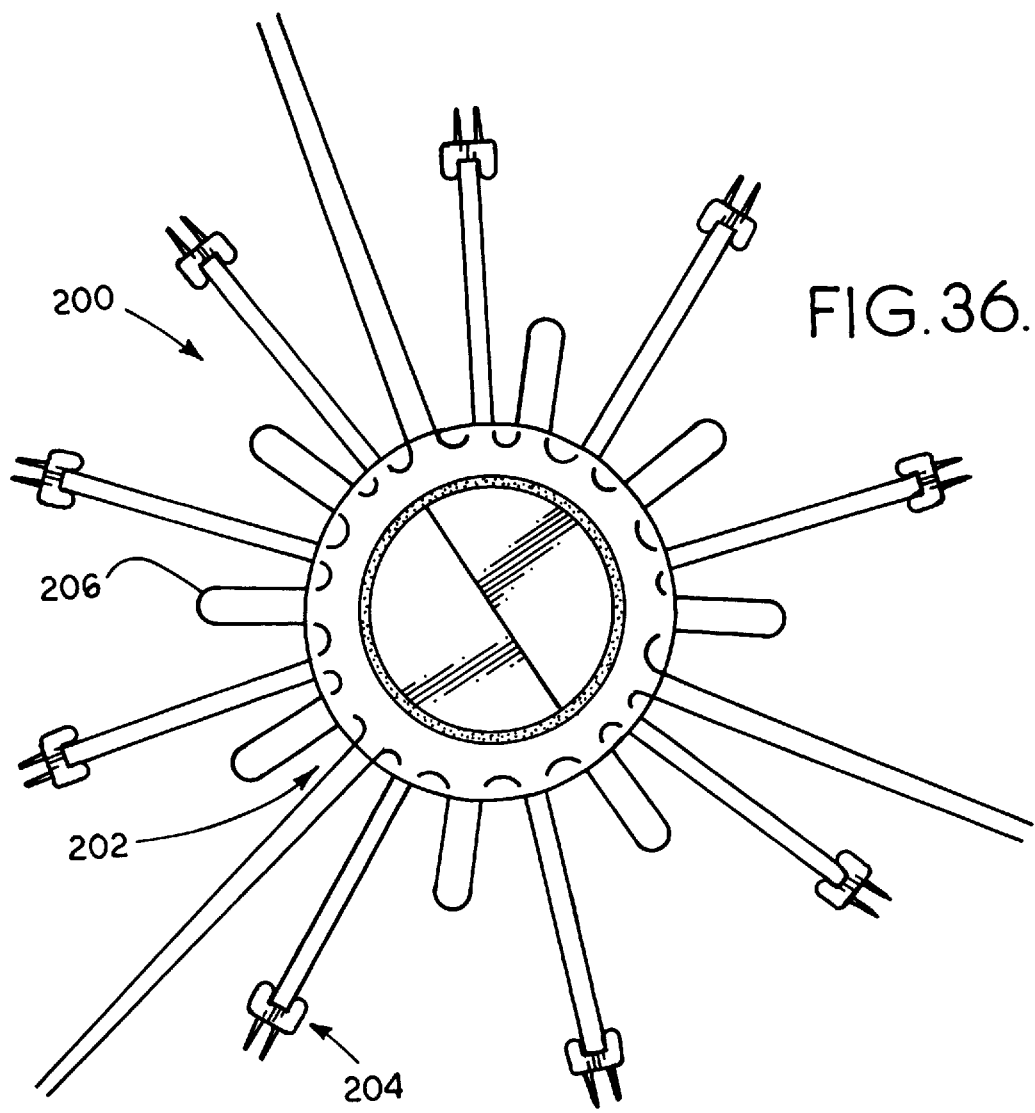
FIG. 36 shows an alternative form of the system in which a running suture has loops to which anchors can be fastened as needed to increase the number of anchor points for a suture.
Figure 37:
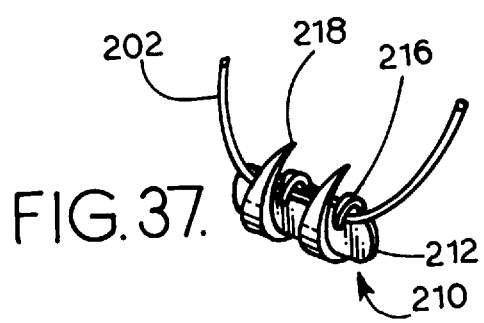
FIG. 37 shows a suture suitable for use on the loops of the suture shown in FIG. 36.

Yet another form of the suture anchor system is shown in FIGS. 36 and 37. Anchor system 200 is amenable to adding additional sutures if the need arises. System 200 includes a valve cuff 202 which will be anchored in place in the manner discussed above, and a first plurality of suture anchors 204 which can be of the forms discussed above. System 200 includes a suture that runs through the cuff and has loops, such as loop 206 that extend out of the cuff. As shown in FIG. 36, the loops are interspaced with the anchors, however, fewer loops can be used if desired without departing from the scope of this disclosure. If more anchors are used than are shown in FIG. 36, additional anchors can be attached to the loops and placed in the manner discussed above. The suture is then pulled taut, and any loops that do not have anchors attached will be pulled into the cuff, while loops that do have anchors will act in the manner discussed above for anchoring the suture. Thus, the surgeon has the option of adding anchors as needed. Anchor 210, shown in FIG. 37, is suitable for use on the loops 202. Anchor 210 includes a base 212 having clips 216 on one edge which are deformed about the suture to attach the anchor to the suture, and tissue pins 218 on the other edge for penetrating the tissue.

It is understood that while certain forms of the present invention have been illustrated and described herein, it is not to be limited to the specific forms or arrangements of parts described and shown.

We claim:

1. A tool for placing a surgical fastener into tissue during a minimally invasive surgical procedure comprising:
    A) a base having a distal end and a proximal end;
    B) a fastener deployment mechanism operating mechanism on said proximal end and which is located outside of a patient during use;
    C) a fastener deployment mechanism on said distal end, a fastener anchor releasably mounted on said fastener deployment mechanism, said fastener anchor having a base and a deformable element on said base;
    D) a first operating element operatively connecting said fastener deployment mechanism to said fastener deployment mechanism operating mechanism to rotate said fastener deployment mechanism for forcing said deformable element through a patient's tissue and forcing said fastener anchor base against the patient's tissue;
    E) a needle grabber element adjacent to said distal end;
    F) a second operating element operatively connected to said needle grabber; and
    G) an anvil located adjacent to said distal end in position to be abuttingly contacted by a deformable element when said fastener deployment mechanism is operated to form said fastener.

2. The tool defined in claim 1 wherein said first operating mechanism includes a driver saddle element pivotally attached to said distal end.

3. The tool defined in claim 2 wherein said driver saddle element further includes two hooks which releasably engage ends of a fastener mounted thereon.

4. The tool defined in claim 2 wherein said base further includes a track for slidably mounting said needle grabber on said base.

5. The tool defined in claim 2 further including a handle for moving said needle grabber.

6. A fastener delivery and deployment mechanism for use in placing fasteners into tissue during a minimally invasive surgical procedure comprising:
    A) a base having a longitudinal axis, a distal end and a proximal end;
    B) an operating mechanism on said proximal end;
    C) a fastener storage and deploying mechanism on said distal end including means for holding fasteners, means for storing a suture, means for forming fasteners and means for gripping a suture needle;
    D) means for operatively connecting said fastener storage and deploying mechanism to said operating mechanism including means to rotate said means for holding fasteners with respect to said distal end perpendicular to said longitudinal axis towards said means for forming fasteners; and
    E) means on said fastener storage and deployment mechanism for releasably holding an anchor, said anchor being attached to a suture and being released from said fastener storage and deployment mechanism to remain in place adjacent to a patient's tissue when said fastener storage and deployment mechanism is removed from the patient after operating to deploy a fastener.

7. The fastener deployment system defined in claim 6 wherein said means for storing a suture further includes a disposable suture storage cartridge releasably mounted on said fastener storage and deploying mechanism.

8. The fastener deployment system defined in claim 6 wherein said anchor includes a base and a deformable fastener element which is forced through the patient's tissue when said fastener storage and deploying mechanism is rotated towards said means for forming fasteners.

9. The fastener deployment system defined in claim 8 wherein said suture needle is located with respect to said anchor to pass through the patient's tissue when said fastener storage and deploying mechanism is rotated towards said means for forming fasteners.

10. The fastener deployment system defined in claim 6 wherein said means for forming fasteners includes an anvil located adjacent to said distal end.

11. The fastener deployment system defined in claim 10 wherein said anvil is operatively connected to said means for operatively connecting said fastener storage and deploying mechanism to said operating mechanism so said anvil is moved towards into position to be abuttingly contacted by said deformable fastener element when said means for holding fasteners is rotated.

12. The fastener deployment system defined in claim 6 further including a suture needle grabber on said distal end in position to be contacted by a suture needle when said means for holding fasteners is rotated.

13. A method of placing a suture in tissue during a minimally invasive surgical procedure comprising:
    A) providing a surgical fastener comprising a one-piece body having a central section, and two prongs extending away from said central section, said central section having a tissue abutting area large enough to anchor said body in place on tissue with said prongs extending through said tissue and at least one length of suture with a needle attached to the fastener with the suture stored for deployment;
    B) releasably mounting said surgical fastener on a distal end of a tool, said tool including a base having a distal end and a proximal end, an operating mechanism on said proximal end and which is located outside of a patient during use, a fastener deployment mechanism on said distal end, an operating element operatively connecting said fastener deployment mechanism to said operating mechanism, a needle grabber element adjacent to said distal end, a second operating element operatively connecting said needle grabber to said operating mechanism, and an anvil located adjacent to said distal end;

C) placing the operating mechanism adjacent to tissue at a selected location;

D) operating said operating mechanism to drive the prongs of the fastener and a suture needle through the tissue;

E) crimping said prong to anchor the fastener to the tissue;

F) grabbing said suture needle; and

G) pulling said suture needle out of said patient.

14. The method defined in claim 13 further including placing a prosthesis on the suture lead and guiding that prosthesis to a selected position in the patient adjacent to said fastener.

15. The method defined in claim 13 further including releasably mounting a cassette on the tool.

16. The method defined in claim 15 further including storing a suture lead in the cassette.

17. The method defined in claim 13 wherein the step of crimping said prong includes rotating said fastener about the distal end of the tool to drive the fastener through the patient's tissue and upwardly towards the anvil after the prong has exited the tissue.

18. A method of placing a suture in tissue during a minimally invasive surgical procedure comprising:

A) providing a surgical fastener comprising a one-piece body having a central section, and two prongs extending away from said central section, said central section having a tissue abutting area large enough to anchor said body in place on tissue with said prongs extending through said tissue;

B) releasably mounting said surgical fastener on a distal end of a tool, said tool including a base having a distal end and a proximal end, an operating mechanism on said proximal end and which is located outside of a patient during use, a fastener deployment mechanism on said distal end, an operating element operatively connecting said fastener deployment mechanism to said operating mechanism;

C) placing the operating mechanism adjacent to tissue at a selected location;

D) operating said operating mechanism to drive the prongs of the fastener through the tissue;

E) crimping said prong to anchor the fastener to the tissue;

F) threading a suture through the tissue; and

G) locating one end of the suture outside of the patient.

19. The method defined in claim 18 further including attaching a sewing cuff to the suture between the ends of the suture.

20. The method defined in claim 13 further including locating a plurality of anchors adjacent to each other and tieing one suture associated with one anchor to a suture associated with an adjacent anchor.

21. The method defined in claim 13 further including locating a plurality of anchors adjacent to each other and tieing one end of a suture associated with one anchor to another end of the suture.

* * * * *